United States Patent
Enoki et al.

(10) Patent No.: US 12,329,458 B2
(45) Date of Patent: Jun. 17, 2025

(54) CONTROL DEVICE, OPHTHALMIC MICROSCOPE SYSTEM, OPHTHALMIC MICROSCOPE, AND IMAGE PROCESSING APPARATUS

(71) Applicant: SONY GROUP CORPORATION, Tokyo (JP)

(72) Inventors: Junichiro Enoki, Tokyo (JP); Tomoyuki Ootsuki, Tokyo (JP); Yoshio Soma, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 756 days.

(21) Appl. No.: 17/430,027

(22) PCT Filed: Feb. 7, 2020

(86) PCT No.: PCT/JP2020/004902
§ 371 (c)(1),
(2) Date: Aug. 11, 2021

(87) PCT Pub. No.: WO2020/170866
PCT Pub. Date: Aug. 27, 2020

(65) Prior Publication Data
US 2022/0115122 A1 Apr. 14, 2022

(30) Foreign Application Priority Data
Feb. 20, 2019 (JP) .................. 2019-028043

(51) Int. Cl.
*A61B 3/14* (2006.01)
*A61B 3/13* (2006.01)
(Continued)

(52) U.S. Cl.
CPC ................ *A61B 3/13* (2013.01); *A61B 90/20* (2016.02); *A61F 9/007* (2013.01);
(Continued)

(58) Field of Classification Search
CPC ....... A61B 3/13; A61B 17/3423; A61B 90/20; A61F 9/007; G02B 21/0004; G02B 21/02;
(Continued)

(56) References Cited

U.S. PATENT DOCUMENTS

2002/0191280 A1 12/2002 Horiguchi et al.
2006/0203330 A1 9/2006 Moeller et al.
(Continued)

FOREIGN PATENT DOCUMENTS

CN 1447146 A 10/2003
CN 109963496 A 7/2019
(Continued)

OTHER PUBLICATIONS

International Search Report and Written Opinion of PCT Application No. PCT/JP2020/004902, issued on Apr. 28, 2020, 15 pages of ISRWO.

*Primary Examiner* — Mahidere S Sahle
(74) *Attorney, Agent, or Firm* — CHIP LAW GROUP

(57) ABSTRACT

[Object] To provide a control device, an ophthalmic microscope system, an ophthalmic microscope, and an image processing apparatus by which setting of a microscope can be assisted.
[Solving Means] A control device according to the present technology includes a control unit. The control unit controls, on the basis of a detection result of a surgical instrument using a captured image of an eye to be examined which is imaged by an image pickup element of an ophthalmic microscope via a front lens, at least one of an imaging condition of the image pickup element or whether or not to perform inversion processing of making an image of a region inverted through the front lens a normal image.

13 Claims, 16 Drawing Sheets

(51) Int. Cl.

| | | |
|---|---|---|
| *A61B 90/20* | (2016.01) | |
| *A61F 9/007* | (2006.01) | |
| *G02B 21/00* | (2006.01) | |
| *G02B 21/02* | (2006.01) | |
| *G02B 21/06* | (2006.01) | |
| *G02B 21/36* | (2006.01) | |
| *G06T 3/60* | (2006.01) | |
| *G06T 7/00* | (2017.01) | |
| *G06T 7/70* | (2017.01) | |
| *G16H 20/40* | (2018.01) | |
| *G16H 30/40* | (2018.01) | |
| *G16H 40/63* | (2018.01) | |
| *H04N 7/18* | (2006.01) | |
| *H04N 13/239* | (2018.01) | |
| *H04N 23/56* | (2023.01) | |
| *H04N 23/69* | (2023.01) | |
| *H04N 23/698* | (2023.01) | |
| *A61B 17/34* | (2006.01) | |

(52) U.S. Cl.
CPC ......... *G02B 21/0004* (2013.01); *G02B 21/02* (2013.01); *G02B 21/06* (2013.01); *G02B 21/361* (2013.01); *G06T 3/60* (2013.01); *G06T 7/0012* (2013.01); *G06T 7/70* (2017.01); *G16H 20/40* (2018.01); *G16H 30/40* (2018.01); *G16H 40/63* (2018.01); *H04N 7/183* (2013.01); *H04N 13/239* (2018.05); *H04N 23/56* (2023.01); *H04N 23/69* (2023.01); *H04N 23/698* (2023.01); *A61B 17/3423* (2013.01); *G06T 2207/10056* (2013.01); *G06T 2207/30041* (2013.01)

(58) Field of Classification Search
CPC ........ G02B 21/06; G02B 21/361; G06T 3/60; G06T 7/0012; G06T 7/70; G06T 2207/10056; G06T 2207/30041; G16H 20/40; G16H 30/40; G16H 40/63; H04N 7/183; H04N 13/239; H04N 23/56; H04N 23/69; H04N 23/698; H04N 23/80
USPC ........ 351/205, 206, 216, 221; 359/368, 385; 600/236, 452, 558; 606/4, 204.25
See application file for complete search history.

(56) References Cited

U.S. PATENT DOCUMENTS

| | | |
|---|---|---|
| 2013/0076020 A1 | 3/2013 | Lucey et al. |
| 2019/0328225 A1 | 10/2019 | Enoki |

FOREIGN PATENT DOCUMENTS

| | | | |
|---|---|---|---|
| DE | 102017121085 B3 | 1/2019 | |
| EP | 3524136 A1 | 8/2019 | |
| EP | 3553584 A1 | 10/2019 | |
| JP | 2001-017459 A | 1/2001 | |
| JP | 2001-108906 A | 4/2001 | |
| JP | 2003-062003 A | 3/2003 | |
| JP | 2006-247399 A | 9/2006 | |
| JP | 2017-217290 A | 12/2017 | |
| JP | 2019-051304 A | 4/2019 | |
| WO | 2018/096763 A1 | 5/2018 | |
| WO | 2018/105411 A1 | 6/2018 | |
| WO | WO-2018217951 A1 * | 11/2018 | ......... A61B 1/00039 |
| WO | 2019/012881 A1 | 1/2019 | |

* cited by examiner

| Situation | | Observation target | Focal position | Inversion processing | Illumination | Magnification (angle of view) | Depth of field |
|---|---|---|---|---|---|---|---|
| Surgical instrument is outside eye to be examined | Setting insertion position of surgical instrument | Trocar | d2 (Long) | Not done | Extraocular illumination | Magnification "a" (wide angle of view) (including exterior of lens) | Deep |
| Surgical instrument is inside eye to be examined | In middle of inserting surgical instrument | Inside lens | d1 (Short) | Done | Intraocular illumination | Magnification "a" (wide angle of view) (including exterior of lens) | Deep |
| | In middle of treatment | Inside lens | d1 (Short) | Done | Intraocular illumination | Magnification "b" (narrow angle of view) (interior of lens only) | Settable by user |
| | In middle of removing surgical instrument | Inside lens | d1 (Short) | Done | Intraocular illumination | Magnification "a" (wide angle of view) (including exterior of lens) | Deep |
| Surgical instrument is outside eye to be examined | After removing surgical instrument | Settable by user | Settable by user | Settable by user | Settable by user | Settable by user | Settable by user |

FIG.7

CONTROL DEVICE, OPHTHALMIC MICROSCOPE SYSTEM, OPHTHALMIC MICROSCOPE, AND IMAGE PROCESSING APPARATUS

CROSS REFERENCE TO RELATED APPLICATIONS

This application is a U.S. National Phase of International Patent Application No. PCT/JP2020/004902 filed on Feb. 7, 2020, which claims priority benefit of Japanese Patent Application No. JP 2019-028043 filed in the Japan Patent Office on Feb. 20, 2019. Each of the above-referenced applications is hereby incorporated herein by reference in its entirety.

TECHNICAL FIELD

The present technology relates to a control device, an ophthalmic microscope system, an ophthalmic microscope, and an image processing apparatus, which are used for ophthalmic surgery.

BACKGROUND ART

In ophthalmic surgery, a unit including a front lens is added and used to an ophthalmic surgical microscope in some cases. Wide-angle observation lenses in retinal vitreous surgery and gonioscopes in minimally invasive glaucoma surgery (MIGS) for treating an angle have been widely used as front lenses.

For example, an ophthalmic surgical microscope to which a wide-angle microscope unit including a wide-angle observation lens is added is suitable for observing a fundus in a wide range. Due to the addition of the wide-angle microscope unit, the focal position changes to a position at which an image is formed by the wide-angle observation lens, which is a front lens, for example, in the ophthalmic surgical microscope. Moreover, an image in the front lens is inversed due to the placement of the front lens. Since various optical conditions in the microscope are changed in this manner due to the addition of the front lens, the microscope needs to be adjusted.

Patent Literature 1 has described detecting the presence or absence of a front lens and accordingly automatically performing various types of adjustment.

CITATION LIST

Patent Literature

Patent Literature 1: Japanese Patent Application Laid-open No. 2017-217290

DISCLOSURE OF INVENTION

Technical Problem

In actual surgery, insertion or removal of a surgical instrument and treatment are conducted in a state in which a front lens is placed in front of an eye to be examined. A user of a microscope needs to set the microscope such that images suitable for each of different situations, for example, at the time of insertion or removal of the surgical instrument and in the middle of treatment.

In view of the above-mentioned circumstances, it is an object of the present technology to provide a control device, an ophthalmic microscope system, an ophthalmic microscope, and an image processing apparatus by which setting of a microscope can be assisted.

Solution to Problem

In order to accomplish the above-mentioned object, a control device according to an embodiment of the present technology includes a control unit.

The control unit controls, on the basis of a detection result of a surgical instrument using a captured image of an eye to be examined which is imaged by an image pickup element of an ophthalmic microscope via a front lens, at least one of an imaging condition of the image pickup element or whether or not to perform inversion processing of making an image of a region inverted through the front lens a normal image.

In accordance with this configuration, the at least one of the imaging condition of the image pickup element or whether or not to perform the inversion processing is automatically set on the basis of the detection result of the surgical instrument.

The ophthalmic microscope may include an optical system that guides an image of the eye to be examined to the image pickup element and an extraocular illumination light source that outputs extraocular illumination light for illuminating the eye to be examined from outside, and the imaging condition may include at least one of a focal position of the optical system or whether or not to perform radiation of the extraocular illumination light.

The control unit may control, on the basis of setting information preset for each situation determined on the basis of the detection result of the surgical instrument, the at least one of the imaging condition of the image pickup element or whether or not to perform the inversion processing.

In terms of the situation, in a case where it is detected that a tip of the surgical instrument is located outside a region of the front lens in the captured image, it may be determined that it is a situation where an insertion position is being set, and in a case where it is detected that the tip of the surgical instrument is located inside the region of the front lens in the captured image, it may be determined that it is a situation where the surgical instrument is located inside the eye to be examined.

The surgical instrument may be insertable into the eye via a trocar placed on the eye to be examined, and in terms of the setting information, in the situation where the insertion position is being set, the focal position may be set to be on the trocar, the inversion processing may be set not to be performed, and the extraocular illumination light may be set to be output, and in the situation where the surgical instrument is being inserted, the focal position may be set to be on the front lens, the inversion processing may be set to be performed, and the extraocular illumination light may be set not to be output.

The ophthalmic microscope further may include an intraocular illuminator that radiates intraocular illumination light to an inside of the eye to be examined, the front lens may be a wide-angle observation lens for observing the inside of the eye to be examined, and in terms of the setting information, in the situation where the insertion position is being set, the intraocular illumination light may be set not to be output, and in the situation where the surgical instrument is being inserted, the intraocular illumination light may be set to be output.

The front lens may be a gonioscope for observing an angle of the eye to be examined.

The control device may further include a memory that records resetting information obtained by the setting information preset for each situation being reset by a user of the ophthalmic microscope, in which the control unit may control the imaging condition of the image pickup element by using the resetting information in preference to the preset setting information in accordance with the determined situation.

The imaging condition may include at least one of a magnification of the optical system or a depth of field of the optical system, and the control unit may control the at least one of the magnification or the depth of field on the basis of the setting information preset for each determined situation.

In terms of the situation, in a case where it is detected that a tip of the surgical instrument is located outside a region of the front lens in the captured image, it may be determined that it is a situation where an insertion position is being set, and in a case where it is detected that the tip of the surgical instrument is located inside the region of the front lens in the captured image, it may be determined that it is a situation where the surgical instrument is located inside the eye to be examined, the situation where the surgical instrument is located inside the eye to be examined may include a situation in the middle of treatment where treatment of the eye to be examined is being performed and a situation not in the middle of treatment where the treatment of the eye to be examined is not being performed, and the control unit may control the at least one of the magnification or the depth of field on the basis of the setting information preset for the determined situation in the middle of treatment or the determined situation not in the middle of treatment.

The situation not in the middle of treatment may include a situation in the middle of insertion that is a movement of the surgical instrument from the insertion position of the eye to be examined to a position for the treatment and a situation in the middle of removal that is a movement of the surgical instrument from the position for the treatment to the outside of the eye to be examined, and the control unit may control the at least one of the magnification or the depth of field on the basis of the setting information preset for the determined situation in the middle of treatment, the determined situation in the middle of insertion, or the determined situation in the middle of removal.

The ophthalmic microscope may further include an inverter that optically performs the inversion processing, and the control unit may control the inverter on the basis of the setting information set for the determined situation.

The control device may further include an image processing unit that performs the inversion processing of inverting a region in the captured image, in which an image is formed through the front lens, to thereby generate a display image, in which the control unit may control the image processing unit on the basis of the setting information set for the determined situation.

In order to accomplish the above-mentioned object, an ophthalmic microscope system according to an embodiment of the present technology includes an ophthalmic microscope and a control device.

The ophthalmic microscope includes a front lens capable of being placed in front of an eye to be examined, an extraocular illumination light source that outputs extraocular illumination light for illuminating the eye to be examined from outside, and an image pickup element that images the eye to be examined.

The control device controls, on the basis of a detection result of a surgical instrument using a captured image of the eye to be examined which is imaged by the image pickup element via the front lens, at least one of an imaging condition of the image pickup element or whether or not to perform inversion processing of making an image of a region inverted through the front lens a normal image.

In order to accomplish the above-mentioned object, an ophthalmic microscope according to an embodiment of the present technology includes a first optical system, a second optical system, a first image pickup element, and a second image pickup element.

The first optical system transmits an image of an eye to be examined and includes a front lens that is placed in front of the eye to be examined.

The second optical system transmits the image of the eye to be examined and does not include the front lens.

On the first image pickup element, the image of the eye to be examined, which is transmitted by the first optical system, is formed in a state in which a focal position of the first optical system is located in a region in which the front lens is located.

On a second image pickup element, the image of the eye to be examined, which is transmitted by the second optical system, is formed in a state in which a focal position of the second optical system is located in a region outside a region of the eye to be examined, in which the front lens is located.

The ophthalmic microscope may further include a second illuminator that radiates second illumination light to the eye to be examined not via the front lens at a time of imaging with the second image pickup element.

The ophthalmic microscope may further include: a first illuminator that radiates first illumination light to an inside of the eye to be examined at a time of imaging with the first image pickup element; and a second illuminator that radiates second illumination light to the eye to be examined at a time of imaging with the second image pickup element, in which the imaging with the first image pickup element and the imaging with the second image pickup element may be alternately performed, the first illuminator may output the first illumination light in synchronization with the imaging with the first image pickup element, and the second illuminator may output the second illumination light in synchronization with the imaging with the second image pickup element.

The ophthalmic microscope may further include a first illuminator that radiates first illumination light having a first wavelength to an inside of the eye to be examined at a time of imaging with the first image pickup element; and a second illuminator that radiates second illumination light having a second wavelength different from the first wavelength to the eye to be examined at a time of imaging with the second image pickup element, in which the first image pickup element may include an image pickup element that selectively receives light having the first wavelength and the second image pickup element includes an image pickup element that selectively receives light having the second wavelength.

The ophthalmic microscope may further include: a first illuminator that radiates first illumination light to an inside of the eye to be examined at a time of imaging with the first image pickup element; and a second illuminator that radiates second illumination light having a second polarization state to the eye to be examined at a time of imaging with the second image pickup element, in which an optical element that allows light having a first polarization state orthogonal to the second polarization state to pass therethrough may be placed in front of the first image pickup element.

In order to accomplish the above-mentioned object, an image processing apparatus according to an embodiment of the present technology includes an image processing unit.

The image processing unit combines a first image and a second image to thereby generate a display image, the first image being obtained by extracting a region of a first captured image, in which a front lens is located, and performing inversion processing only on the extracted region, the first captured image being acquired by a first image pickup element of an ophthalmic microscope, the second image being constituted by a region of a second captured image, which is other than the region in which the front lens is located, the second captured image being acquired by a second image pickup element of the ophthalmic microscope, the ophthalmic microscope including the front lens capable of being placed in front of an eye to be examined, the first image pickup element that adjusts a focal position onto the front lens and images the eye to be examined, and the second image pickup element that adjusts a focal position onto a region of the eye to be examined outside a region, in which the front lens is located and images the eye to be examined.

In order to accomplish the above-mentioned object, an ophthalmic microscope system according to an embodiment of the present technology includes an ophthalmic microscope and an image processing apparatus.

The ophthalmic microscope includes a front lens capable of being placed in front of an eye to be examined, a first image pickup element that adjusts a focal position onto the front lens and images the eye to be examined, and a second image pickup element that adjusts a focal position onto a region of the eye to be examined outside a region, in which the front lens is located and images the eye to be examined.

The image processing apparatus includes an image processing unit that combines a first image and a second image to thereby generate a display image, the first image being obtained by extracting a region of a first captured image, in which the front lens is located, and performing inversion processing only on the extracted region, the first captured image being acquired by the first image pickup element, the second image being constituted by a region of a second captured image, which is other than the region in which the front lens is located, the second captured image being acquired by the second image pickup element.

BRIEF DESCRIPTION OF DRAWINGS

FIG. 7 A diagram for describing setting information for each situation of the microscope of the ophthalmic microscope system.

MODE(S) FOR CARRYING OUT THE INVENTION

First Embodiment

An ophthalmic microscope system according to a first embodiment of the present technology will be described. Here, retinal vitreous surgery using a wide-angle observation lens as a front lens will be described as an example.

In this embodiment, an example in which a user of an ophthalmic microscope such as an ophthalmologist and an assistant can perform observation and surgery while viewing an image captured by an image pickup element on a display device instead of looking through the microscope will be described. A display image that is an operative field image obtained by performing processing such as color enhancement on a captured image acquired by an image pickup element 181 mounted on a microscope body 11 to be described later is displayed on the display device.

In an ophthalmic microscope system 100 according to this embodiment, a situation is determined on the basis of a surgical instrument detection result using a captured image of an eye to be examined that is an operative field. Then, the microscope is controlled in accordance with the determined situation, and, more specifically, the imaging condition of the image pickup element, whether or not to perform inversion processing, or the like is controlled in accordance with the determined situation.

It should be noted that the present technology can also be applied to an ophthalmic microscope system in which observation or surgery is performed by observation through the eyepiece of a microscope by a user without using the display device. In this case, the captured image acquired by the image pickup element 181 is used for the surgical instrument detection used for the situation determination.

[Configuration of Ophthalmic Microscope System]

Figure 1:
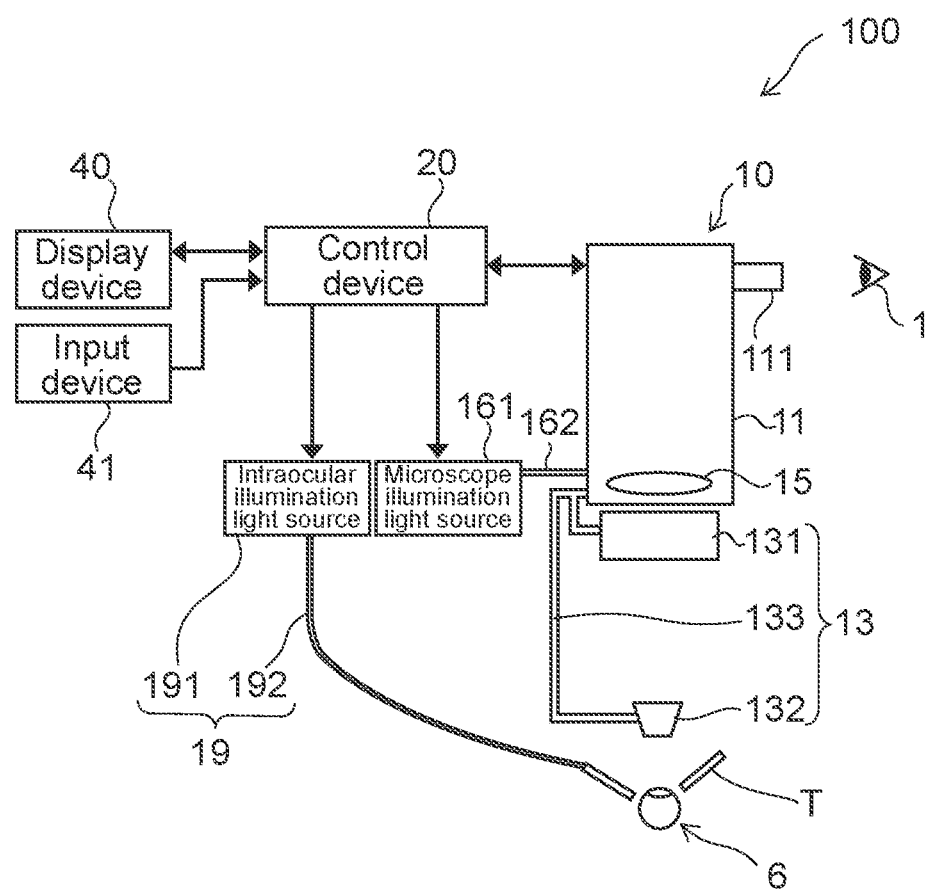
FIG. 1 A schematic diagram of an ophthalmic microscope system according to a first embodiment of the present technology.

FIG. 1 is a schematic diagram showing a configuration of the ophthalmic microscope system (hereinafter, referred to as microscope system) 100 according to this embodiment.

As shown in FIG. 1, the microscope system 100 includes an ophthalmic microscope (hereinafter, referred to as microscope) 10, a control device 20, a display device 40, and an input device 41.

The microscope 10 is used by a user of the microscope system 100 to observe a magnified image of the eye to be examined 6 in an examination or surgery in the ophthalmologic field. In the figure, the reference sign 1 denotes an eye of the user of the microscope 10. The user can perform examination or surgery while viewing a display image displayed on the display device 40. The eye to be examined 6 is a patient's eye on which examination or surgery is to be performed.

As shown in FIG. 1, the microscope 10 includes a microscope body 11 having an observation barrel 111, a contactless wide-angle observation unit 13 as a function expansion unit, a microscope illumination light source 161 as an extraocular illumination light source, and an intraocular illuminator 19.

The microscope 10 may be an optical microscope having a general configuration.

Two observation barrels 111 are provided for both the left and right eyes, though not limited thereto. The details of the microscope 10 will be described later.

The control device 20 controls the microscope 10 by using the captured image acquired by the image pickup element 181 to be described later mounted on the microscope 10. Moreover, the control device 20 performs image processing on the captured image and generates a display image to be displayed on the display device 40.

The details of the control device 20 will be described later.

The display device 40 displays a display image formed by performing image processing by the control device 20 on the basis of the captured image acquired by the image pickup element 181. The display device 40 is a general display or a head-mounted display. Alternatively, the display device 40 may be a plurality of displays and can be a display for a surgeon and a display for an assistant, for example.

The input device 41 is an input interface to the microscope system 100. The user can input body information of the patient, various types of information regarding the surgery, and the like via the input device 41. Moreover, for example, the user can input an instruction to change various settings regarding the microscope according to the situation, and the like via the input device 41.

The type of the input device 41 is not limited, and the input device 41 may be any of various known input devices. A mouse, a keyboard, a touch panel, a switch, a foot switch, a lever, or the like can be applied as the input device 41, for example. In a case where the touch panel is used as the input device 41, the touch panel may be provided on the display surface of the display device 40.

Additionally, the input device 41 may include a microphone capable of collecting the user's voice, and various inputs may be performed by voice through the microphone. By configuring the input device 41 to be capable of inputting various types of information without contact in this manner, it is possible for the user belonging to a particularly clean area to operate a device belonging to a non-clean area without contact. Moreover, the user can operate the device without releasing his or her hand from the surgical instrument that the user holds, to thereby improve the convenience of the user.

Figure 3:
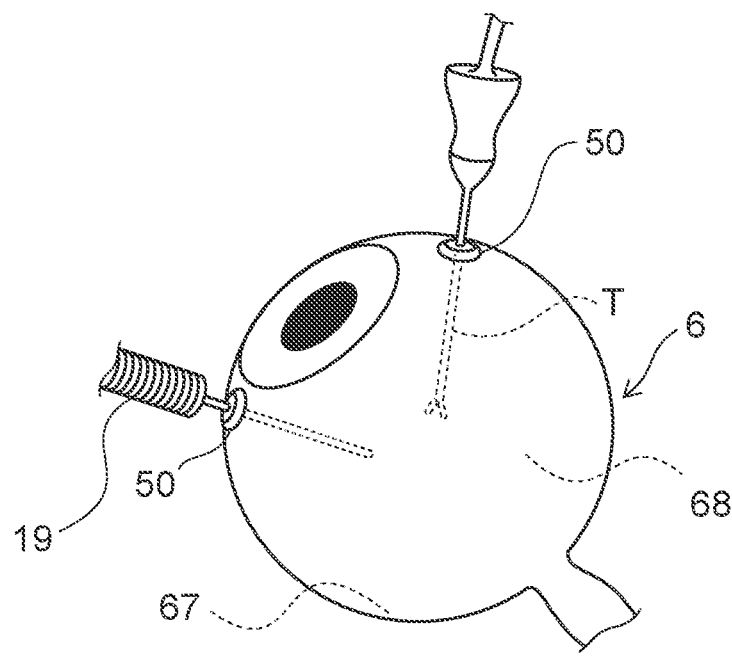
FIG. 3 A schematic diagram showing a state of surgery of an eye that is an observation target of the ophthalmic microscope system.
Figure 4:
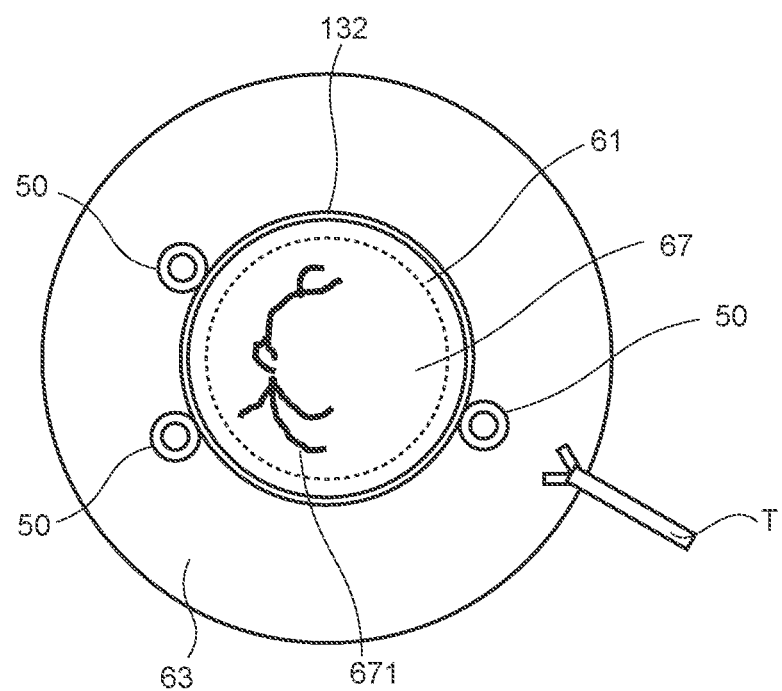
FIG. 4 A schematic diagram showing a state of the surgery of the eye that is the observation target of the ophthalmic microscope system and a plan view as the eye on which a front lens and trocars are placed is viewed from the front side.

FIGS. 3 and 4 are schematic diagrams showing a state of the retinal vitreous surgery in the microscope system 100. FIGS. 3 and 4 show a surgical instrument T used for surgery of an eye. FIG. 3 is a schematic perspective view of an eyeball of the eye to be examined 6 and shows a state in which the intraocular illuminator 19 and the surgical instrument T have been inserted into the eye and not showing a front lens 132. FIG. 4 corresponds to a diagram as viewed from the front side of the eye to be examined 6, in which the front lens 132 is placed in front of the eye to be examined 6, and shows a state before the intraocular illuminator 19 and the surgical instrument T are inserted.

Figure 5:
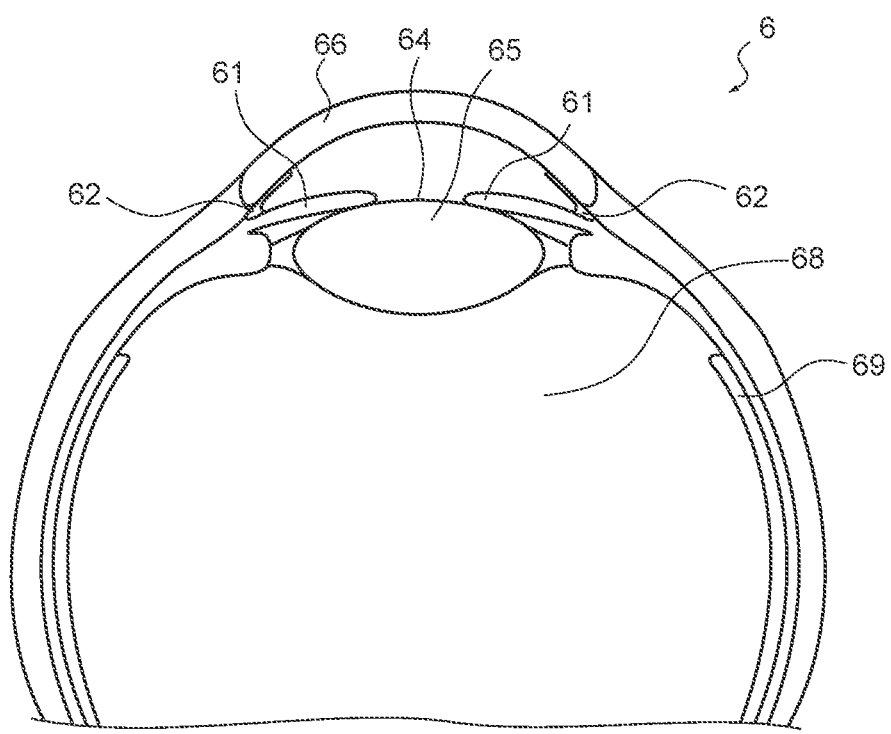
FIG. 5 A cross-sectional view of the eye.

FIG. 5 is a partial cross-sectional view of the eye to be examined 6.

A instrument suitable for a treatment at that time is used as for the surgical instrument T. For example, the surgical instrument T may be a vitreous cutter, forceps, a backflush needle, internal limiting membrane (ILM) forceps, a laser device for photocoagulating the retina, or the like. Since the access range is limited by port positions for insertion of surgical instruments, and the surgical instrument T is inserted and removed as appropriate to perform treatment by using two ports typically.

As shown in FIGS. 4 and 5, the eye to be examined 6 includes tissues such as an iris 61, a crystalline lens 65, and a cornea 66. On the surface of the crystalline lens 65, a pupil 64 is located in the middle of the iris 61 and an angle 62 is located at the periphery of the cornea 66. A vitreous body 68 is a jelly-like tissue that occupies the larger part of the eyeball from behind the crystalline lens 65 to a retina 69. In FIG. 4, the reference sign 671 denotes a blood vessel of a fundus 67.

Since observation of the fundus 67 is required in the retinal vitreous surgery, the intraocular illuminator 19 is, as shown in FIG. 3, inserted into the eye to be examined 6, the intraocular illumination is performed, and then the surgical instrument T is inserted into the eye for performing the surgery. The intraocular illuminator 19, the vitreous cutter for resecting and absorbing the vitreous body, and a cylindrical trocar 50 serving as a guide for introducing and withdrawing a tube (not shown) for injecting a perfusate for maintaining the shape of the eyeball during the surgery are placed on the eye to be examined 6.

As shown in FIGS. 3 and 4, the trocar 50 is placed in the region of the white 63 of the eye around the iris 61 of the eye to be examined 6. The front lens 132 is provided to overlap the cornea when the front lens 132 is placed in front of the eye to be examined 6. In the wide-angle observation using the contactless wide-angle observation unit 13, the fundus 67 is observed, and therefore the pupil 64 is observed in a state in which it is very close to the edge of the front lens 132.

[Configuration of Ophthalmic Microscope]

Next, the microscope 10 will be described.

Figure 2:
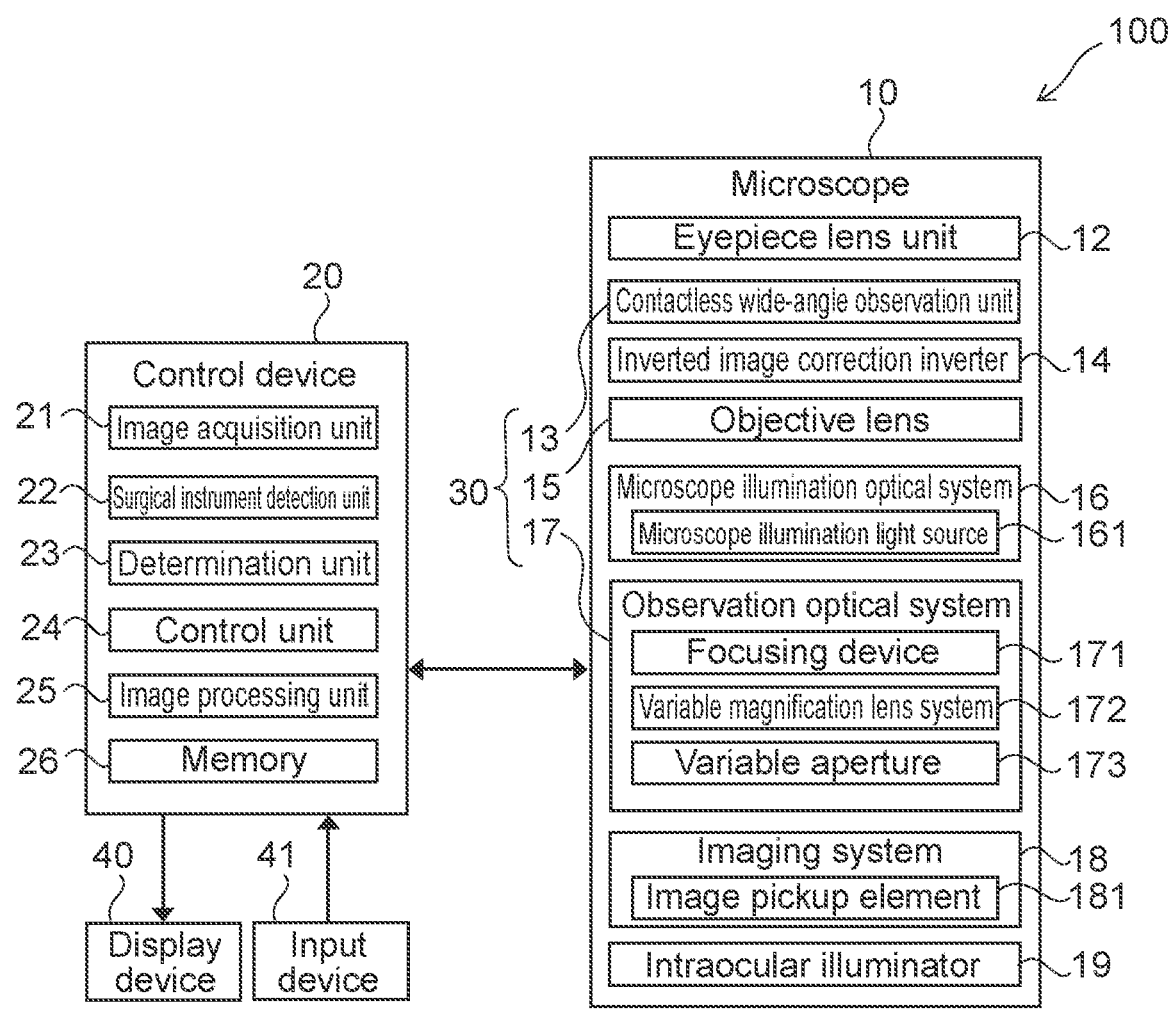
FIG. 2 A block diagram of the ophthalmic microscope system.

FIG. 2 is a block diagram of the microscope system 100.

As shown in FIG. 2, the microscope 10 includes an eyepiece lens unit 12, the contactless wide-angle observation unit 13, an inverted image correction inverter 14, an objective lens 15, a microscope illumination optical system 16, an observation optical system 17, an imaging system 18, and the intraocular illuminator 19.

The eyepiece lens unit 12 further magnifies the image produced by the observation optical system 17 for observing the image with the eyes.

The contactless wide-angle observation unit 13 is a function expansion unit provided to be capable of being inserted and removed into/from the microscope body 11.

Figure 6A:
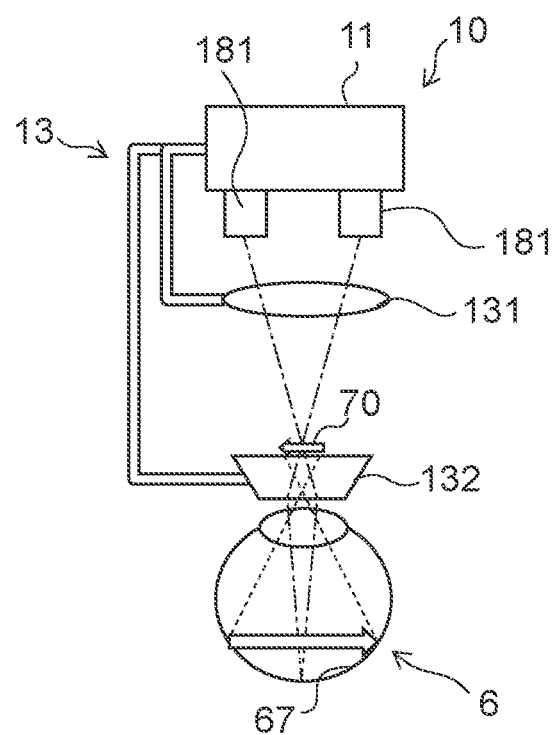
FIGS. 6A and 6B Schematic diagrams of a microscope of the ophthalmic microscope system and a diagram describing a case where the front lens is placed on an optical path and a case where the front lens is not placed on an optical path.
Figure 6B:
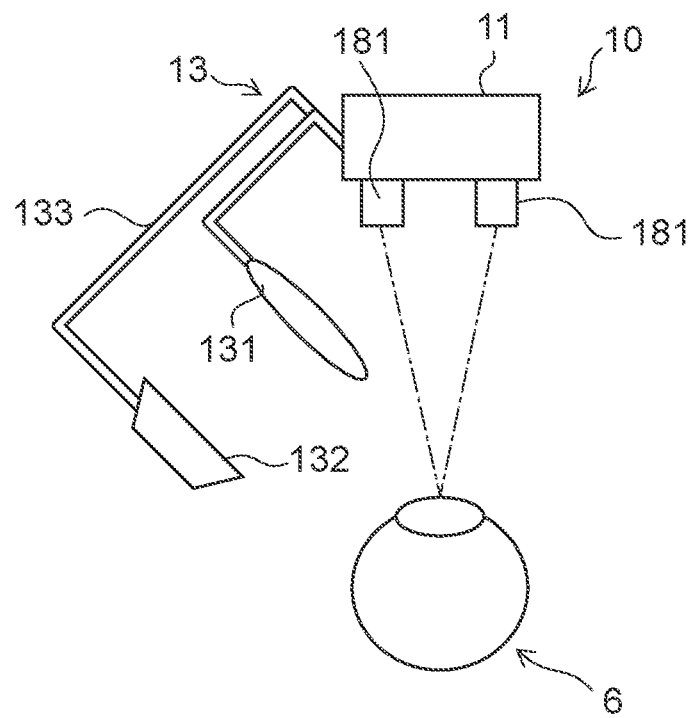

FIG. 6A shows a case where the front lens 132 of the contactless wide-angle observation unit 13 is located on an observation optical path and FIG. 6B shows a case where the front lens 132 of the contactless wide-angle observation unit 13 is not located on the observation optical path.

As shown in FIGS. 1, 6A and 6B, the contactless wide-angle observation unit 13 is placed between the objective lens 15 and the eye to be examined 6. The contactless wide-angle observation unit 13 includes a reduction lens 131, a front lens 132, and a holding arm 133. The reduction lens 131 and the front lens 132 are held by the holding arm 133.

The holding arm 133 is configured to be movable in a state in which the holding arm 133 is mounted on the microscope body 11. As shown in FIGS. 6A and 6B, the movement of the holding arm 133 can position the reduction lens 131 and the front lens 132 on the observation optical path or remove the reduction lens 131 and the front lens 132 therefrom.

In this embodiment, a wide-angle observation lens is used as the front lens 132, and the fundus of the eye to be examined 6 can be observed by using the contactless wide-angle observation unit 13.

As shown in FIG. 6 A, the front lens 132 generates an intermediate image in which the fundus 67 is inverted on an intermediate image plane 70. Placing the front lens 132 in the optical path makes it possible to observe the fundus of the eye to be examined 6.

The reduction lens 131 amplifies the refractive power of the objective lens 15. The reduction lens 131 is aligned with the intermediate image plane 70 by displacing the focal plane of the observation optical path of the microscope 10.

The microscope body 11 houses the inverted image correction inverter 14, the objective lens 15, a part of the microscope illumination optical system 16, the observation optical system 17, and the imaging system 18.

The inverted image correction inverter 14 performs inversion processing of returning the inverted image to the normal image through the front lens 132.

The inverted image correction inverter 14 is controlled on the basis of a control signal generated by the control device 20.

The microscope illumination optical system 16 serving as an extraocular illumination optical system illuminates the eye to be examined 6 through the objective lens 15.

The microscope illumination optical system 16 is divided into a microscope illumination optical system for the user's left eye and a microscope illumination optical system for the user's right eye. In the following description, unless it is particularly necessary to distinguish between the one for the right eye and the one for the left eye, the microscope illumination optical system will be referred to as the microscope illumination optical system 16.

As shown in FIGS. 1 and 2, the microscope illumination optical system 16 includes the microscope illumination light source 161 and an optical fiber 162, which are placed outside the microscope body 11, and a condenser lens, a collimating lens, and a reflection mirror, which are housed in the microscope body 11 and not shown in the figures.

The microscope illumination light source 161 emits illumination light for illuminating the eye to be examined 6 from the outside of the eye to be examined 6 during examination, surgery, or the like.

One end of the optical fiber 162 is connected to the microscope illumination light source 161 and the other end of the optical fiber 162 is connected to the microscope body 11.

The illumination light output from the microscope illumination light source 161 (extraocular illumination light) is guided by the optical fiber 162, enters the condenser lens, becomes a parallel light beam through the collimating lens. The parallel light beam is reflected by the reflection mirror toward the objective lens 15, passes through the objective lens 15, and is radiated to the eye to be examined 6. The illumination light radiated to the eye to be examined 6 is reflected and scattered by tissues of the eye to be examined 6 such as the cornea 66 and the retina 69.

The reflected and scattered return light passes through the objective lens 15 and enters the observation optical system 17 when the contactless wide-angle observation unit 13 is not located on the observation optical path. On the other hand, when the contactless wide-angle observation unit 13 is located on the observation optical path, the return light passes through the front lens 132, the reduction lens 131, the objective lens 15 and enters the observation optical system 17.

The intraocular illuminator 19 is provided outside the microscope body 11 and illuminates the inside of the eye to be examined 6.

The intraocular illuminator 19 includes an intraocular illumination light source 191 and an optical fiber 192.

The intraocular illumination light source 191 emits illumination light (intraocular illumination light) for radiating the inside of the eye to be examined 6 for retinal vitreous surgery or the like requiring observation of the fundus in a wide range.

One end of the optical fiber 192 is connected to the intraocular illumination light source 191 and the other end of the optical fiber 192 is inserted into the inside of the eye to be examined 6.

As shown in FIG. 3, the illumination light output from the intraocular illumination light source 191 is guided by the optical fiber 192 and is emitted from the other end of the optical fiber 192 to the inside of the eye to be examined 6.

Whether or not to output the illumination light from the microscope illumination light source 161 and whether or not to output the illumination light from the intraocular illumination light source 191 are controlled on the basis of a control signal output from the control device 20.

The observation optical system 17 is for observing, through the objective lens 15, the eye to be examined 6 illuminated by the microscope illumination optical system 16 and the intraocular illuminator 19. The observation optical system 17 transmits a projected image of the eye to be examined 6 to the eye 1 of the user or the image pickup element 181 to be described later.

The contactless wide-angle observation unit 13, the objective lens 15, and the observation optical system 17 constitutes a transmission optical system 30 that is an optical system for transmitting the image of the eye to be examined 6 to the image pickup element 181. The transmission optical system 30 is an optical system that forms an image of the return light (the image of the eye to be examined 6) from the eye to be examined 6 on the image pickup element 181.

The transmission optical system 30 includes a first transmission optical system and a second transmission optical system.

The first transmission optical system is constituted by the front lens 132, the reduction lens 131, the objective lens 15, and the observation optical system 17.

The second transmission optical system is constituted by the reduction lens 131, the objective lens 15 and the observation optical system 17. The return light from the eye to be examined 6 includes return light that does not pass through the front lens 132, passes through the reduction lens 131, the objective lens 15, and the observation optical system 17, and enters the image pickup element 181. The optical system for transmitting the return light that does not pass through the front lens 132 to the image pickup element 181 will be referred to as the second transmission optical system.

It should be noted that unless it is necessary to distinguish between the first transmission optical system and the second transmission optical system, the transmission optical system will be sometimes referred to as the transmission optical system 30.

The observation optical system 17 is divided into an observation optical system for the user's left eye and an observation optical system for the user's right eye and each have an observation optical path. Unless it is particularly necessary to distinguish between the one for the right eye and the one for the left eye, the observation optical system will be referred to as the observation optical system 17.

The observation optical system 17 includes a focusing device 171, a variable magnification lens system 172 including a plurality of zoom lenses, an imaging lens (not shown), a variable aperture 173, a beam splitter (not shown).

The focusing device 171 can move the microscope 10 up and down. Accordingly, the operation interval between the objective lens 15 and the patient's eye to be examined 6 can be adjusted, and the microscope 10 is focused on a region to be examined of the eye to be examined 6. Therefore, it is possible to control the focal position of the transmission optical system 30 by controlling the focusing device 171.

The plurality of zoom lenses of the variable magnification lens system 172 is movable along the optical axis of the observation optical system. The movement of the plurality of zoom lenses changes the magnification in the captured image of the eye to be examined 6. Therefore, by controlling the variable magnification lens system 172, it is possible to control the magnification of the transmission optical system 30 and to control the angles of view of the captured image and the display image.

The depth of field of the transmission optical system 30 depends on the focal length of the lens, the F-value, and the imaging distance. Therefore, it is possible to control the depth of field of the transmission optical system 30 by controlling the focusing device 171 and the variable aperture 173.

The control of the focal position of the transmission optical system 30, the control of the magnification (angle of view), and the control of the depth of field are performed on the basis of a control signal output from the control device 20.

As described above, the illumination light radiated to the eye to be examined 6 is reflected and scattered by the tissues of the eye to be examined 6 such as the cornea 66 and the retina 69. The reflected and scattered return light passes through the front lens 132, the reduction lens 131, the objective lens 15 and enters the observation optical system 17.

The return light entering the observation optical system 17 is controlled in terms of the magnification by the variable magnification lens system 172, passes through the imaging lens and the variable aperture 173, and enters the beam splitter. The beam splitter guides part of the return light to the imaging system 18 and guides the other part of the return light to the eyepiece lens unit 12. The return light entering the eyepiece lens unit 12 makes observation through the eyepiece possible.

The imaging system 18 includes the imaging lens (not shown), the image pickup element 181, and the like. The image pickup element 181 includes, for example, an image sensor such as a charge coupled device (CCD) and a complementary metal oxide semiconductor (CMOS) and the like. The light receiving surface of the image pickup element 181 is placed at a position optically conjugate with the focal position of the objective lens 15.

Figure 8:
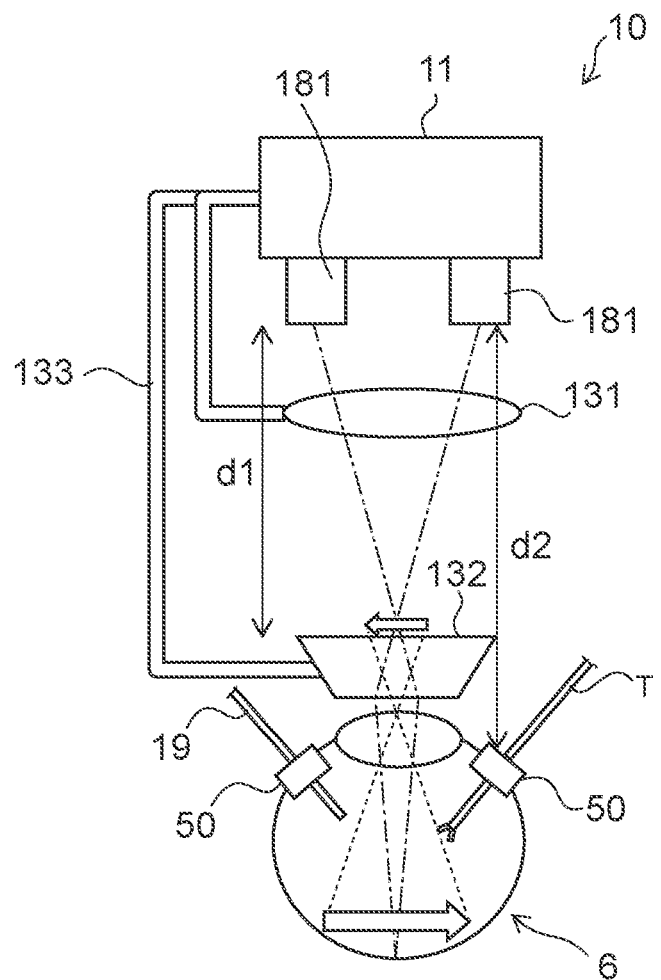
FIG. 8 A schematic diagram showing a state of the surgery of the eye using the ophthalmic microscope system.

The imaging system 18 may be associated with both the left and right observation optical systems 17 or may be associated with either one of the left and right observation optical systems 17. In this embodiment, the imaging system 18 is associated with both the left and right ones, and two image pickup elements 181 respectively provided in the left and right imaging systems are shown in FIG. 8 to be described later. Since the image pickup elements 181 are provided for each of the left and right ones in this embodiment in this manner, a captured image that is a stereo image can be obtained.

The image pickup elements 181 are each mounted on the microscope 10 and capable of imaging the eye through the front lens 132, the reduction lens 131 and the observation optical system 17. The captured image captured by the image pickup element 181 is output to the control device 20.

It should be noted that the display device is provided for the example of using the HUS system in this embodiment, though the display device is not necessarily required in a microscope system in which observation and surgery are performed by observation through the eyepiece, and the captured image acquired by the image pickup element 181 is used for surgical instrument detection for situation determination.

[Configuration of Control Device]

Next, the control device 20 will be described.

The control device 20 performs surgical instrument detection by using the captured image acquired from the microscope 10, determines a situation on the basis of the surgical instrument detection result, and controls the microscope 10 on the basis of setting information set for each situation in advance according to the determined situation. More specifically, the control device 20 controls at least one of the imaging condition of the image pickup element 181 or whether or not to perform the inversion processing on the basis of the setting information. In addition, for the imaging condition, at least one of the focal position of the transmission optical system 30 or whether or not to perform the output of the microscope illumination light source 161 (with or without the illumination light) is controlled.

In this embodiment, on the basis of the setting information preset for the determined situation, the control device 20 generates a control signal for controlling the focal position of the transmission optical system 30, whether or not to perform the inversion processing by the inverted image correction inverter 14, and whether or not to perform the output of the microscope illumination light source 161 and the intraocular illumination light source 191, and outputs the control signal to the microscope 10.

On the basis of the control signal, the control of the focusing device 171 of the observation optical system 17, the control of whether or not to perform the inversion processing by the inverted image correction inverter 14, the control of whether or not to perform the radiation of the illumination light from the microscope illumination light source 161, and the control of whether or not to perform the radiation of the illumination light from the intraocular illumination light source 191 are performed at the microscope 10.

As shown in FIG. 2, the control device 20 includes an image acquisition unit 21, an surgical instrument detection unit 22, a determination unit 23, a control unit 24, an image processing unit 25, and a memory 26.

The image acquisition unit 21 acquires the captured image captured by the image pickup element 181 from the microscope 10.

The surgical instrument detection unit 22 detects the presence or absence of the surgical instrument T by using the acquired captured image. Known techniques such as an object recognition technique using feature points, detection using machine learning, detection using markers provided in the surgical instrument, and detection using motion vectors with information in the time direction can be used for the detection of the surgical instrument T using the captured image.

In addition, in a case of detecting the presence of the surgical instrument T, the surgical instrument detection unit 22 detects the tip of the surgical instrument T. An object recognition technique, detection using machine learning, detection using markers, and the like can be used for the detection of the tip position as in the detection of the presence or absence of the surgical instrument T. In a case where the detection is performed using those techniques, the detection of the presence of the surgical instrument T and the detection of the tip of the surgical instrument T may be performed simultaneously.

In a case where the detection of the presence of the surgical instrument T and the detection of the tip of the surgical instrument T are performed separately, detection using edge information and color information, detection by removal of the region of the surgical instrument T using parallax information in a case where the stereo image is used, and the like can be used for the detection of the presence of the surgical instrument T in addition to the above-mentioned techniques.

In addition to the above-mentioned techniques, the following technique can be used for the detection of the tip of the surgical instrument T. That is, in a case where the surgical instrument T is present in the captured image, a linear region of the surgical instrument T extending from the image outer peripheral portion toward the image center portion is detected in the captured image, and therefore, it is possible to detect that an end of the extracted region of the surgical instrument T, which is opposite to an end of the extracted region of the surgical instrument T, which is located near the image outer peripheral portion, is the tip of the surgical instrument T.

In addition, the surgical instrument detection unit 22 detects the tip position of the surgical instrument T. More specifically, the surgical instrument detection unit 22 detects whether or not the tip of the surgical instrument T is located inside a region of the captured image in which the front lens 132 is supposed to be located.

The determination unit 23 determines a situation on the basis of the detection result of the surgical instrument detection unit 22.

The determination unit 23 determines that it is a situation where the surgical instrument is absent on the basis of the detection result made by the surgical instrument detection unit 22 that the surgical instrument T is not present.

The determination unit 23 determines that it is a situation where the surgical instrument T is located inside the eye to be examined 6 on the basis of the detection result made by the surgical instrument detection unit 22 that the tip of the surgical instrument T is located inside the region (inside the region of the front lens) in the captured image in which the front lens 132 is estimated to be located.

The determination unit 23 determines that it is a situation where the insertion position of the surgical instrument T is being set on the basis of the detection result made by the surgical instrument detection unit 22 that the tip of the surgical instrument T is located outside the region (outside the region of the front lens) in the captured image in which the front lens 132 is estimated to be located. The situation where the insertion position of the surgical instrument T is being set is a situation where the surgical instrument T has not yet been inserted into the eye to be examined 6.

Here, the region in the captured image in which the front lens 132 is estimated to be located may be recorded in advance. Since the front lens 132 is fixed to the microscope body 11, it is possible to estimate in which range of the captured image the front lens 132 is located if the magnification is determined. The region of the captured image in which the front lens 132 is estimated to be located may be recorded for each magnification, and the region of the captured image in which the front lens 132 is estimated to be located is changed by changing the magnification.

In addition, the determination unit 23 determines whether it is a situation where the surgical instrument T is being inserted into the eye to be examined 6, is being removed, or is performing treatment on the basis of trajectory information of the tip of the surgical instrument T. In this manner, the situation where the surgical instrument T is located inside the eye to be examined 6 may be further divided into three situations: a situation in the middle of insertion; a situation in the middle of treatment; and a situation in the middle of removal, and the three situations may be determined, and it will be described in a second embodiment to be described later.

It should be noted that in the description of an operation of the control device 20 using the flowcharts of FIGS. 10 and 11, which will be described later, an example in which a situation where the insertion position of the surgical instrument T is being set and a situation where the surgical instrument T is located inside the eye to be examined 6 are determined will be described.

In this manner, whether or not the surgical instrument T is located inside the eye to be examined 6 can be determined by using XY coordinates of the tip position of the surgical instrument T.

Alternatively, in a case where the captured image is the stereo image, the tip position of the surgical instrument T may be detected using a Z coordinate indicating depth information obtained from parallax information of two captured images for the left eye and the right eye. More specifically, since inversion through the front lens 132 makes a captured image in which the tip of the surgical instrument T is located in front of the front lens 132, it may be determined by using the Z coordinate that the surgical instrument T is located inside the eye to be examined 6 in a case where the tip of the surgical instrument T is located in front of the front lens 132 in the captured image.

Moreover, in addition to the detection using the Z coordinate, the tip position of the surgical instrument T may be detected using the XY coordinates, to thereby improve the detection accuracy.

Moreover, the determination unit 23 may determine that the surgical instrument is absent on the basis of the detection result by the surgical instrument detection unit 22 that the surgical instrument is absent and may add the "situation where the surgical instrument is absent" as a determination item.

The memory 26 stores setting information for each situation preset. The setting information for each situation will be described later.

The memory 26 may record the determination result of the situation by the determination unit 23 in time series.

The memory 26 may record resetting values adjusted and reset by the user in time series in association with the situation at that time. The use of the resetting value recorded in the memory 26 will be described in the second embodiment to be described later.

The control unit 24 generates a control signal regarding the microscope 10 on the basis of the setting information regarding the microscope 10 which is preset for each situation on the basis of the determination result by the determination unit 23, and outputs the control signal to the microscope 10.

The image processing unit 25 generates a display image obtained by performing image processing such as color enhancement on the captured image acquired by the image acquisition unit 21 and outputs the display image to the display device 40.

Here, the microscope 10 needs to set, for each situation at that time, the focal position of the transmission optical system 30, the magnification (angle of view) of the transmission optical system 30, the depth of field of the transmission optical system 30, whether or not to perform the inversion processing, whether or not to perform the illumination, and the like, for example.

Regarding the focal position, it is essential to focus on the trocar 50 when the insertion position of the surgical instrument T is set.

In the middle of inserting the surgical instrument in which the surgical instrument T is being inserted into the eye to be examined 6 after the insertion position of the surgical instrument T is determined, it is desirable to focus on the front lens 132 in order to correctly observe the surgical instrument which is being inserted.

In order to correctly observe the inside of the front lens that is the operative field in the middle of treatment, it is essential to focus on the region in which the front lens 132 is located.

In the middle of removing the surgical instrument, it is essential to focus the surgical instrument on the region in which the front lens 132 is located in order to correctly observe the surgical instrument which is being removed.

It should be noted that after the removal, the user can arbitrarily set the focal in a manner that depends on which part of the eye to be examined 6 the user wishes to observe.

Moreover, regarding the inversion processing, the inversion processing of the inverted image in the front lens is not performed in order to observe the trocar 50 placed outside the region in which the front lens 132 is located at the time of setting the insertion position of the surgical instrument T.

In the middle of inserting the surgical instrument in which the surgical instrument T is being inserted into the eye to be examined 6 after the insertion position of the surgical instrument T is determined, it is essential to perform the inversion processing such that the inverted image in the front lens becomes the erect image in order to correctly observe the surgical instrument which is being inserted.

In the middle of treatment, it is essential to perform the inversion processing such that the inverted image in the front lens becomes the erect image in order to correctly observe the inside of the front lens that is the operative field.

In the middle of removing the surgical instrument, it is essential to perform inversion processing such that the inverted image in the front lens becomes the erect image in order to correctly observe the surgical instrument which is being removed.

It should be noted that after the removal, the user can arbitrarily set whether or not to perform the inversion processing in a manner that depends on which part of the eye to be examined 6 the user wishes to observe.

Moreover, regarding the illumination, it is essential to turn on the extraocular illumination in order to observe the trocar 50 until the tip of the surgical instrument T fits into the trocar 50 at the time of setting the insertion position of the surgical instrument T.

In the middle of inserting the surgical instrument in which the surgical instrument T is being inserted into the eye to be examined 6 after the insertion position of the surgical instrument T is determined, it is desirable to turn on the intraocular illumination in order to observe the surgical instrument which is being inserted and to turn off the extraocular illumination in order to eliminate the specular reflection of light on the surface of the front lens 132.

In the middle of treatment, it is desirable to turn on the intraocular illumination to observe the fundus and the surgical instrument and to turn off the extraocular illumination to eliminate specular reflection of light at the surface of the front lens 132.

In the middle of removing the surgical instrument, it is desirable to turn on the intraocular illumination in order to observe the fundus and the surgical instrument and to turn off the extraocular illumination in order to eliminate the specular reflection of light on the surface of the front lens 132.

It should be noted that after removing the surgical instrument, the user can arbitrarily set the intraocular illumination to remain on in a case where the user wishes to observe the inside of the eye as it is. Alternatively, in order to avoid retinal light damage, the intraocular illumination may be set to be turned off once by the user or automatically.

Moreover, regarding the magnification (angle of view), it is desirable to set the magnification to have a wide angle of view in order to observe both the region in which the trocar 50 is located and the region in which the front lens 132 is located at the time of setting the insertion position of the surgical instrument. Thus, in addition to the region in which the front lens 132 is located, the outside of the front lens 132 in which the trocar 50 is placed can be also checked with the captured image, the display image.

It is desirable to set the magnification to have a wide angle of view in order to observe both the trocar 50 and the inside of the front lens 132 in the middle of inserting the surgical instrument in which the surgical instrument T is being inserted into the eye to be examined 6 after the insertion position of the surgical instrument T is determined.

In the middle of treatment, it is not necessarily necessary to observe the trocar 50, and therefore it is desirable to set the angle of view narrower than that at the time of setting the insertion position of the surgical instrument and in the middle of inserting the surgical instrument.

In the middle of removing the surgical instrument, it is desirable to set the angle of view wide enough to allow observation from the entire fundus to the trocar 50 for the sake of safe operation.

It should be noted that after removing the surgical instrument, the user can arbitrarily set the magnification (angle of view) in a manner that depends on which part of the eye to be examined 6 the user wishes to observe.

Moreover, in the depth of field, it is unnecessary to consider the resolution as important at the time of setting the insertion position of the surgical instrument and in the middle of inserting the surgical instrument. Moreover, it is desirable that the depth of field be deeper at the time of setting the insertion position of the surgical instrument and in the middle of inserting the surgical instrument in order to reduce the need for adjustment when the focal position changes from the trocar 50 into the front lens 132 in accordance with the change from the situation of setting the insertion position of the surgical instrument to the situation in the middle of inserting the surgical instrument.

Since it is necessary to consider the resolution and brightness as important in order to know the precise state of the operative field in the middle of treatment, the depth of field is generally expected to be set to be shallower, though it is desirable that the user can arbitrarily set the depth of field.

Since it is important to be able to observe a wide range of the fundus inside the eye in the middle of removing the surgical instrument, it is desirable to set the depth of field to be deeper while balancing the depth of field with the brightness.

Since observation is basically performed after removing the surgical instrument, it is desirable to set the depth of field to be deeper while balancing the depth of field with the brightness as in the middle of removal.

As described above, there are also settings to be desirably performed in a manner that depends on the situation in addition to the settings to be essentially changed, the setting of the microscope is complicated, and it is very troublesome for the user to perform these settings for each situation during the surgery.

In this embodiment, the setting of the microscope is automatically performed on the basis of the surgical instrument detection result using the captured image. More specifically, the situation is determined on the basis of the surgical instrument detection result, and various settings of the microscope 10 are automatically performed on the basis of the setting information preset for each determined situation.

The setting information includes the imaging condition of the image pickup element and whether or not to perform the inversion processing of making the image of the region inverted by the front lens 132 the normal image.

The imaging condition includes the focal position of the transmission optical system 30, the illumination, the magnification (angle of view) of the transmission optical system 30, the depth of field of the transmission optical system 30, and the like.

In the first embodiment, an example in which the focal position of the transmission optical system 30 is set by the control of the focusing device 171. In the second embodiment, an example in which in addition to the setting of the focal position, the magnification of the transmission optical system 30 is set by the control of the variable magnification lens system 172 and the depth of field of the transmission optical system 30 is set by the control of the focusing device 171 and the variable aperture 173 will be described.

FIG. 7 is a diagram for describing the setting information of the microscope 10 for each preset situation.

FIG. 7 shows five situations: a situation at the time of setting the insertion position of the surgical instrument; a situation in the middle of inserting the surgical instrument; a situation in the middle of treatment; a situation in the middle of removing the surgical instrument; and a situation after removing the surgical instrument.

FIG. 8 is a schematic diagram for describing a state of the eye surgery using the microscope system 100.

In FIG. 7, the extraocular illumination refers to irradiation of illumination light (extraocular illumination light) from the microscope illumination light source 161 and irradiation of illumination light (intraocular illumination light) from the intraocular illuminator 19 is off. The intraocular illumination refers to irradiation of illumination light (intraocular illumination light) from the intraocular illuminator 19, and the inside of the eye to be examined 6 is illuminated with the illumination light, and irradiation of illumination light (extraocular illumination light) from the microscope illumination light source 161 is off.

As shown in FIG. 7, the five situations are classified into two situations of a situation where the surgical instrument T is located outside the eye to be examined 6 (the surgical instrument is outside the eye to be examined) and a situation where the tip of the surgical instrument T is located inside the eye to be examined (the surgical instrument is inside the eye to be examined).

The situation where the surgical instrument is outside the eye to be examined includes the situation at the time of setting the insertion position of the surgical instrument and the situation after removing the surgical instrument. In this situation, the surgical instrument T is not located inside the eye to be examined 6 and the surgical instrument T is located outside the eye to be examined 6. In this case, the tip of the surgical instrument T is located outside the region of the captured image in which the front lens 132 is located.

On the other hand, the situation where the surgical instrument is inside the eye to be examined includes three situations: a situation in the middle of inserting the surgical instrument; a situation in the middle of treatment; and a situation in the middle of removing the surgical instrument. In this situation, the surgical instrument T is located inside the eye to be examined 6. In this case, the tip of the surgical instrument T is located in the region of the captured image in which the front lens 132 is located.

As shown in FIG. 7, in this embodiment, the user's setting is possible because the focal, whether or not to perform the inversion processing, the setting of the illumination, the magnification (angle of view), and the depth of field differ in a manner that depends on which part of the eye to be examined 6 the user wishes to view after removing the surgical instrument.

In the microscope system 100, it is sufficient that at least one of the focal position, the inversion processing, or the illumination is automatically controlled. In this embodiment, an example in which the focal position, the inversion processing, and the illumination are automatically controlled will be described.

As shown in FIG. 7, in the situation in the middle of inserting the surgical instrument, the situation in the middle of treatment, and the situation in the middle of removing the surgical instrument, the setting information regarding the focal position, the inversion processing, and the illumination is the same. Therefore, in a case where the focal position, the inversion processing, and the illumination are controlled in accordance with the situation, it is only necessary to determine which of the two situations of the situation at the time of setting the insertion position of the surgical instrument (immediately before inserting the surgical instrument) and the situation where the surgical instrument is inside the eye to be examined it is.

Hereinafter, a case where the microscope 10 is controlled by determining whether it is the situation at the time of setting the insertion position of the surgical instrument (immediately before inserting the surgical instrument) or the situation where the surgical instrument is inside the eye to be examined will be described.

The magnification (angle of view) of the transmission optical system 30 and the control of the depth of field will be described in the second embodiment to be described later.

In the microscope system 100 according to this embodiment, it is determined from the result of surgical instrument detection using the captured image whether it is a situation where the surgical instrument is outside the eye to be examined, which is also the situation at the time of setting the insertion position of the surgical instrument, or the situation where the surgical instrument is inside the eye to be examined.

Depending on the determined situation, on the basis of information (setting information) regarding the focal position preset for each situation, the inversion processing, and the control of the illumination, the focusing device 171, the inverted image correction inverter 14, the microscope illumination light source 161, and the intraocular illumination light source 191 are automatically controlled, and the focal position, whether or not to perform the inversion processing, and whether or not to perform the illumination are set.

In this manner, the microscope system 100 can assist the user in setting the microscope 10. In the microscope system 100, the microscope 10 is automatically controlled in accordance with the determined situation to obtain a display image suitable for the determined situation, and therefore it is possible to reduce the user's labor involved in setting the microscope 10.

As shown in FIG. 7, in the situation at the time of setting the insertion position of the surgical instrument, the trocar 50 serving as a guide for insertion of the surgical instrument T becomes an observation target.

As shown in FIGS. 4 and 8, the trocar 50 is placed outside the region in which the front lens 132 is located as the eye to be examined 6 in front of which the front lens 132 is placed is viewed from the front side.

As shown in FIGS. 7 and 8, the value of the distance from the object-side principal point of the objective lens 15 of the microscope 10 to the trocar 50, which makes the focal position on the trocar 50, is set as the setting information regarding the focal position at the time of setting the insertion position of the surgical instrument, and the setting value is d2 mm. In this embodiment, the distance d2 mm is a preset setting value and is a default value determined with a generally-used value.

It should be noted that in a case where the trocar 50 is not used, the value of the distance from the object-side principal point of the objective lens 15 to the surface of a region in which the front lens 132 of the eye to be examined 6 is not located is set to d2 mm.

Based on this setting information, the control unit 24 automatically controls the focusing device 171 of the observation optical system 17 such that the distance from the object-side principal point of the objective lens 15 to the trocar 50 is to be d2 mm.

Thus, the transmission optical system 30, more particularly, the focal position of the second transmission optical system is set to be on the trocar 50. The state in which the focal position of the second transmission optical system is the trocar 5 is a state in which the front focal position of the objective lens 15 is set to be located on the trocar 50.

The setting information regarding the inversion processing in the situation at the time of setting the insertion position of the surgical instrument is not the inversion processing. Based on this setting information, the control unit 24 controls the inverted image correction inverter 14 so as not to perform the inversion processing.

The setting information regarding the illumination in the situation at the time of setting the insertion position of the surgical instrument indicates that the intraocular illumination is absent and the extraocular illumination is present. Based on this setting information, the control unit 24 controls the radiation of the illumination light from the microscope illumination light source 161 is turned on and the radiation of the illumination light from the intraocular illuminator 19 is turned off.

As shown in FIG. 7, in the situation where the surgical instrument is inside the eye to be examined, a region in the front lens 132 is an observation target.

As shown in FIG. 7 and FIG. 8, the value of the distance from the object-side principal point of the objective lens 15 of the microscope 10 to the front lens 132, which makes the focal position on the front lens 132, is set as the setting information regarding the focal position of the situation where the surgical instrument is inside the eye to be examined, and the setting information is d1 mm. In this embodiment, the distance d1 mm is a preset setting value and is a default value determined with a generally-used value. d1 is a value smaller than d2.

Based on this setting information, the control unit 24 automatically controls the focusing device 171 of the observation optical system 17 such that the distance from the object-side principal point of the objective lens 15 to the front lens 132 to be d1 mm.

Thus, the transmission optical system 30, more particularly, the focal position of the first transmission optical system is set to be on the front lens 132.

The state in which the focal position of the first transmission optical system is on the front lens 132 is in the following state. That is, the relative positional relationship among the objective lens 15, the front lens 132, and the eye to be examined 6 is adjusted such that the position of the back focal point of the front lens 132 coincides with the position of the front focal point of the objective lens 15 and that the fundus 67 is focused.

The setting information regarding the inversion processing in the situation where the surgical instrument is inside the eye to be examined indicates that the inversion processing is to be done. Based on this setting information, the control unit 24 controls the inverted image correction inverter 14 to perform the inversion processing.

The setting information regarding the illumination in the situation where the surgical instrument is inside the eye to be examined indicates that the intraocular illumination is present and the extraocular illumination is absent. Based on this setting information, the control unit 24 controls the radiation of the illumination light from the microscope illumination light source 161 is turned off and the radiation of the illumination light from the intraocular illuminator 19 to be turned on.

Since the focal position, whether or not to perform the inversion processing, and whether or not to perform the illumination are automatically set on the basis of the setting information preset in accordance with the situation as described above, the user is not bothered with the setting of the microscope 10.

It should be noted that regarding the focal position, after the distance from the object-side principal point of the objective lens 15 to the trocar 50 (the front lens 132) is automatically set to be d2 mm (d1 mm), the focal position can be finely adjusted by the user as appropriate and the operative field more suitable for the user can be obtained. Also in such a case, the focal position is automatically preset to the standard position, and therefore the time spent for setting can be greatly shortened as compared to the case where the user performs the setting manually from the beginning.

Moreover, a resetting value newly set by fine adjustment by the user may be recorded in the memory 26.

[Operation of Control Device]

Figure 9:
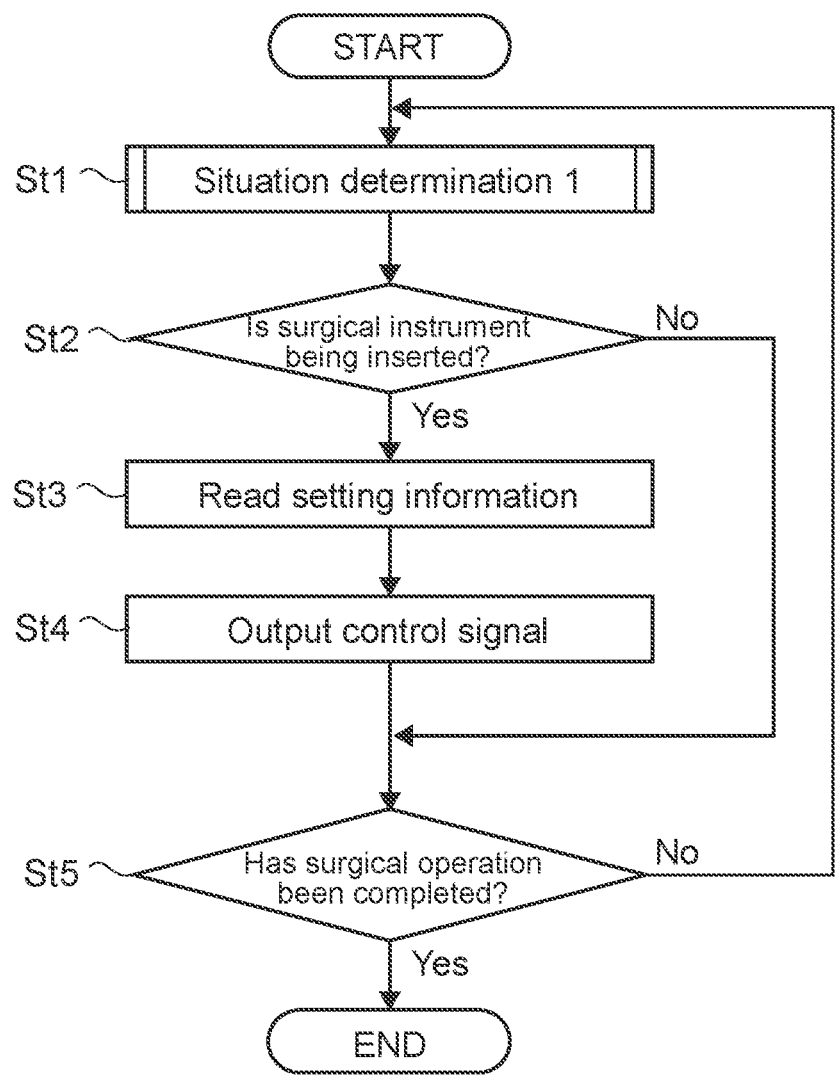
FIG. 9 A flowchart showing an operation of a control device of the ophthalmic microscope system.

FIG. 9 is a flowchart showing the operation of the control device 20.

When the front lens 132 is placed on the observation optical path, the control unit 24 reads from the memory 26 preset setting information associated with the situation of setting the insertion position of the surgical instrument, which is shown in FIG. 7. The setting information is the setting value associated with the focal position, whether or not to perform the inversion processing, and whether or not to perform the illumination. Next, the control unit 24 outputs a control signal generated on the basis of the read setting information to the microscope 10.

In the microscope 10, the focal position of the transmission optical system 30 is controlled to be on the trocar 50 on the basis of the control signal output from the control device 20. Moreover, the inverted image correction inverter 14 is controlled not to perform the inversion processing. Moreover, the output of the illumination light from the intraocular illumination light source 191 and the microscope illumination light source 161 is controlled such that the extraocular illumination is present.

Next, as shown in FIG. 9, first, the processing of a situation determination 1 is performed (St1). FIG. 10 is a flowchart regarding the situation determination 1.

Figure 10:
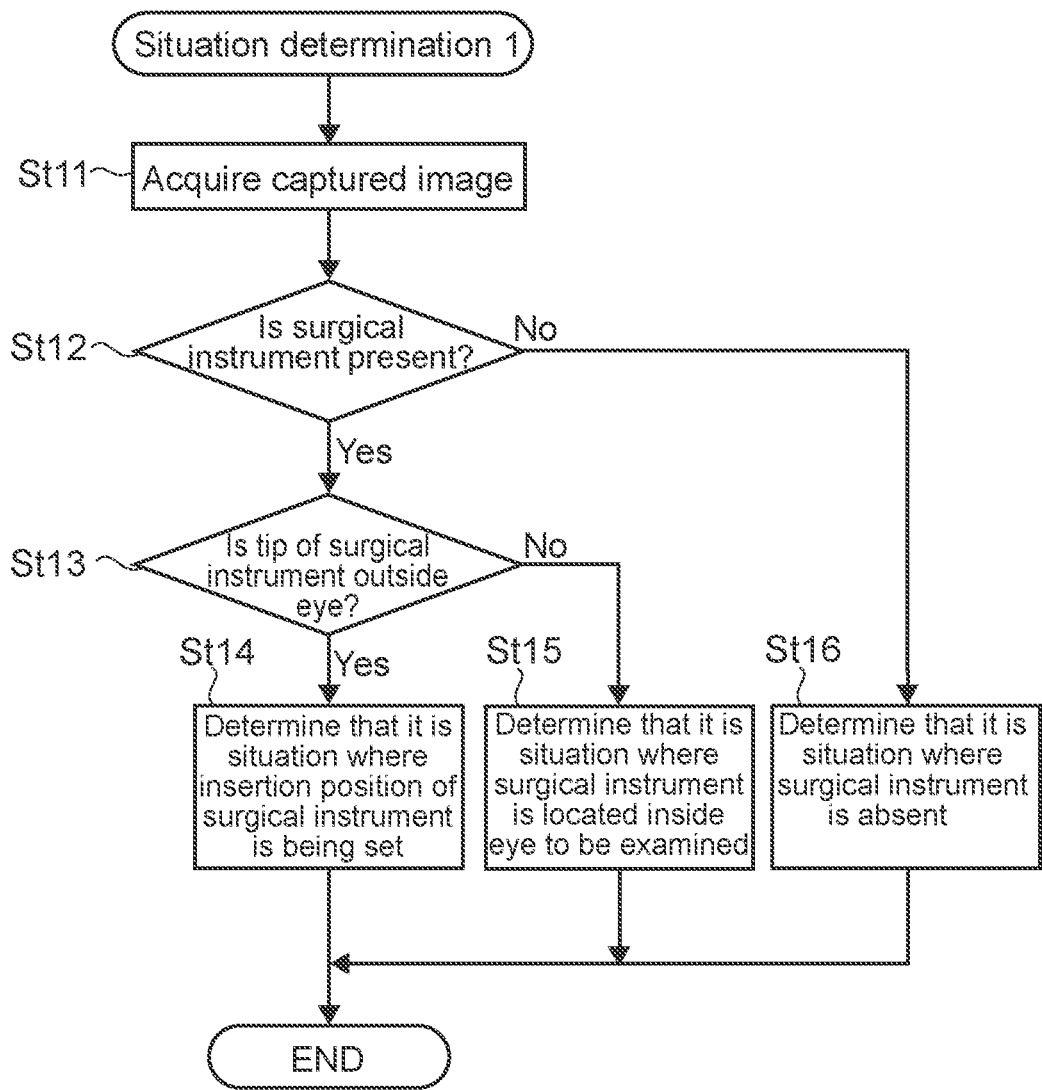
FIG. 10 A flowchart showing an operation of a situation determination 1 at St1 shown in FIG. 9.

As shown in FIG. 10, the image acquisition unit 21 acquires a captured image captured by the image pickup element 181 of the microscope 10 (St11).

Next, the surgical instrument detection unit 22 detects the surgical instrument T in the image using the acquired captured image (St12). In a case where the presence of the surgical instrument T is detected by the surgical instrument detection unit 22, the processing proceeds to St13. In a case where the presence of the surgical instrument T is not detected by the surgical instrument detection unit 22, the processing proceeds to St16.

In St16, the determination unit 23 determines that it is a situation where the surgical instrument T is absent on the basis of the detection result made by the surgical instrument detection unit 22 that the surgical instrument T is absent.

In St13, the surgical instrument detection unit 22 detects the tip position of the surgical instrument T and detects whether or not the tip of the surgical instrument T is located outside the eye to be examined 6.

In a case where the detection result indicates that the tip of the surgical instrument T is located outside the eye to be examined 6 (YES), the determination unit 23 determines that it is the situation at the time of setting the insertion position of the surgical instrument T (St14).

It should be noted that also in the situation after removing the surgical instrument T, the tip of the surgical instrument T is located outside the eye to be examined 6, but for example, in the case where the situation determined immediately before is not the situation where the surgical instrument is inside the eye to be examined, it can be determined that the situation is the situation at the time of setting the insertion position. On the other hand, in the case where the situation determined immediately before is a situation where the surgical instrument is inside the eye to be examined, it can be determined that it is after the removal. In this case, the situation determined by the determination unit 23 is recorded in the memory 26 in time series and the situation determined immediately before can be known using the recorded information.

In a case where the detection result indicates that the tip of the surgical instrument T is not located outside the eye to be examined 6 (NO), the determination unit 23 determines that the surgical instrument T is being inserted into the eye to be examined 6 (St15).

As described above, the situation determination 1 (St1) is performed, and the processing proceeds to St2 below.

Referring back to FIG. 9, in St2, the determination unit 23 determines whether or not the surgical instrument T is being inserted into the eye to be examined 6 on the basis of the determined situation. In a case where it is determined that it is a situation where the surgical instrument T is being inserted (YES), the processing proceeds to St3 (YES). In a case where it is determined that it is not the situation where the surgical instrument T is being inserted (NO), the processing proceeds to St5.

In St3, the control unit 24 reads from the memory 26 preset setting information associated with the situation where the surgical instrument T shown in FIG. 7 is being inserted. The setting information is the setting value associated with the focal position, whether or not to perform the inversion processing, and whether or not to perform the illumination. Next, the control unit 24 outputs to the microscope 10 a control signal generated on the basis of the read setting information.

In the microscope 10, the focal position of the transmission optical system 30 is controlled to be in the front lens 132 on the basis of the control signal output from the control device 20. Moreover, the inverted image correction inverter 14 is controlled to perform the inversion processing. Moreover, the output of the illumination light from the intraocular illumination light source 191 and the microscope illumination light source 161 is controlled such that the intraocular illumination is present.

Next, the determination unit 23 determines whether or not the surgical operation has been completed (St5).

The determination that the surgical operation has been completed is made, for example, by an input operation signal from the input device 41 such as a foot switch by the user being received by the control device 20.

In a case where it is determined that the surgical operation has been completed (YES), the series of processing ends. In a case where it is determined that the surgery is not completed (NO), the processing returns to St1 and the processing is repeated.

In the above description, the setting value such as d1 mm or d2 mm that is the setting information regarding the focal position is a default value including a preset, generally-used value, though not limited thereto. For example, the setting value set by the user may be used or the resetting value finely adjusted and reset by the user and recorded in the memory 26 may be used.

In the second embodiment to be described later, an example in which in addition to the focal position, the inversion processing, and the illumination, the magnification (angle of view) and the depth of field are also controlled on the basis of the setting value (setting information) preset for each situation will be described. Also in the second embodiment, an example in which the setting values of the magnification (angle of view) and the depth of field are default values including preset, generally-used values will be given. However, in the same way as the focal position, it may be the setting value set by the user or may use the resetting value finely adjusted and reset by the user and recorded in the memory 26.

Moreover, the setting information may be set on the basis of the captured image acquired by the image pickup element 181. Specific examples include extracting the region of the front lens 132 from the captured image and setting the magnification (angle of view) such that the region of the front lens 132 occupies X % of the captured image as an area ratio in the XY coordinates (X is a preset numerical value or a numerical value set by the user), detecting the trocar or a conjunctional vessel in the captured image and setting the focal position to bring into focus so as to adjust the peak thereon, and the like.

In addition to the setting items such as the focal position, the inversion processing, the illumination, the magnification (angle of view), and the depth of field, which are shown in FIG. 7, the illumination intensity, the degree of image enhancement of the display image, and the like may be set for each situation. In the same way as the focal point, the magnification (angle of view), and the depth of field, those setting values may be default values including generally-used values or may be setting values set by the user or may use resetting values finely adjusted and reset by the user and recorded in the memory 26.

Additionally, driving of the surgical instrument T may be added as another setting item, and ON/OFF of the driving of the surgical instrument T may be set for each situation. For example, in a case where a vitreous cutter is used as the surgical instrument T, setting information can be used for locking the rotational driving of the vitreous cutter in a situation where the vitreous cutter is being inserted and in a situation where the vitreous cutter is being removed, so as not to prevent the vitreous cutter from rotating in the middle of inserting the vitreous cutter into the eye to be examined 6 and in the middle of removing the vitreous cutter. This makes it possible to improve the safety of the surgery without unnecessarily driving the surgical instrument T other than in the middle of treatment.

Moreover, the example in which the setting information of the microscope is automatically changed on the basis of the surgical instrument detection result using the captured image acquired by the image pickup element has been described hereinabove, though not limited thereto.

For example, the control unit 24 may detect a situation on the basis of an input operation such as the user's operation by a foot switch, an operation switch, or a voice and output a control signal to the microscope 10 in accordance with the detected situation such that setting information preset for each situation is reflected on the microscope. For example, the operation of the foot switch may be used to switch between two manners of control: control according to the situation of setting the insertion position of the surgical instrument; and control according to the situation where the surgical instrument is inside the eye to be examined.

In this manner, the situation may be detected by the user's input operation without detecting the surgical instrument and the microscope 10 may be controlled on the basis of the setting information preset for each situation in accordance with the detected situation.

It should be noted that in this configuration, the detection of the situation is performed by the user's input operation, and therefore the display device and the image pickup element are not necessarily required in the microscope system that performs observation and surgery by observation through the eyepiece.

Moreover, another example is as follows.

Although the example in which the focal position, the inversion processing, and the illumination are automatically changed on the basis of the surgical instrument detection result has been described above, the following configuration may be employed. That is, the configuration may be made such that the switching between the ON/OFF of the illumination is performed by the user, the situation is determined by the switching between the ON/OFF of the illumination, and the focal position and whether or not to perform the inversion processing preset for each situation are performed automatically in accordance with the determined situation.

More specifically, in a case where it is detected that the user changes the extraocular illumination from ON to OFF and changes the intraocular illumination from OFF to ON, the determination unit 23 determines that it is a situation where the surgical instrument T is located inside the eye. Then, on the basis of the setting information preset for each situation, the control unit 24 generates a control signal for controlling the microscope 10 such that the distance from the object-side principal point of the objective lens 15 to the front lens 132 is d1 mm and that the inversion processing is performed and outputs the control signal to the microscope 10.

In this manner, the setting information of the microscope may be changed on the basis of the switching of the illumination by the user without detecting the surgical instrument.

It should be noted that in this configuration, the situation is determined by the illumination operation by the user and the focal position of the microscope and whether or not to perform the inversion processing are automatically controlled in accordance with the determination result, and therefore the display device and the image pickup element are not necessarily required in the microscope system that performs observation and surgery by observation through the eyepiece.

Additionally, for the focal point, the magnification (angle of view), the depth of field, the illumination intensity, the degree of image enhancement of the display image, and the like, the setting values (setting information) preset for each situation may be able to be finely adjusted by the user. Accordingly, a display image more suitable for the user can be obtained.

In this case, when the adjustment is performed by the user and the resetting value is set, the changed resetting value may be configured to be necessarily reflected, and the change of the setting information using the surgical instrument detection result may be configured not to be necessarily reflected each time. Accordingly, fine adjustment is performed by the user, the reset setting value is not overwritten, and the examination and surgery can be performed in a state in which the setting of the microscope is stable.

For example, the change of the setting information using the surgical instrument detection result is not reflected unless it is determined that the surgical instrument is not located inside the eye to be examined after it is determined that the surgical instrument is located inside the eye to be examined.

Accordingly, the setting value according to the control of the microscope is not unnecessarily changed except for the user's adjustment in the middle of treatment.

Moreover, as another example, the setting information based on the surgical instrument detection result is not reflected unless a predetermined time has elapsed after the user's setting is reflected.

It ensures that the setting value is not changed unnecessarily frequently after the user performs fine adjustment.

As described above, the microscope system according to this embodiment can assist the setting work of the microscope and the user can observe the eye to be examined with an appropriate display image without being bothered with the setting of the microscope.

Second Embodiment

In the description of the operation of the control device using the flowchart of the first embodiment, the example in which the situation at the time of setting the insertion position of the surgical instrument T and the situation where the surgical instrument is located inside the eye to be examined are determined has been described.

In this embodiment, a description will be given of an operation of the control device in a case where the situation where the surgical instrument is located inside the eye to be examined is further divided into three situations: a situation in the middle of treatment; a situation in the middle of inserting the surgical instrument; and a situation in the middle of removing the surgical instrument and the three situations are determined.

Moreover, in this embodiment, an example in which the angle of view and the depth of field in the microscope 10 for each situation is controlled in addition to the control of the focal position, the inversion processing, and the illumination described in the first embodiment will be shown.

Moreover, in this embodiment, an example in which the setting value is finely adjusted by the user and the resetting value adjusted and reset by the user is recorded will be described.

Hereinafter, configurations similar to those of the above-mentioned embodiment will be denoted by similar the reference signs and descriptions thereof will be omitted in some cases. Moreover, since the setting information of the focal position, the inversion processing, and the illumination is similar to that of the first embodiment, and the description thereof will be omitted.

In a case where the situation where the surgical instrument is located inside the eye to be examined is divided into three situations: a situation in the middle of treatment; a situation in the middle of inserting the surgical instrument; and a situation in the middle of removing the surgical instrument and the three situations are determined, the determination unit 23 determines the three situations by using trajectory information of the tip of the surgical instrument T, which is detected by using the captured image acquired by the surgical instrument detection unit 22 over time.

More specifically, the determination unit 23 determines that it is the situation in the middle of inserting the surgical instrument in a case where the surgical instrument detection unit 22 detects that the tip of the surgical instrument T is located inside the front lens 132 in the captured image and that the movement of the tip of the surgical instrument T is a movement made continuously from the outside to the inside in the region of the front lens 132.

The determination unit 23 determines that the surgical instrument is being removed in a case where the surgical instrument detection unit 22 detects that the tip of the surgical instrument T is located inside the front lens 132 in the captured image and the movement of the tip of the surgical instrument T is a movement made continuously from the inside to the outside in the region of the front lens 132.

The determination unit 23 determines that it is the situation in the middle of treatment in which the treatment of the eye to be examined 6 is being performed in a case where the surgical instrument detection unit 22 detects that the tip of the surgical instrument T is located inside the front lens 132 in the captured image and that the movement of the tip of the surgical instrument T is neither the movement made continuously from the inside to the outside nor the movement made continuously moving from the outside to the inside in the region of the front lens 132.

Moreover, the determination unit 23 compares the determined situation with the situation determined immediately before and determines whether or not the situation has changed.

In a case where the determination unit 23 determines that the situation has changed, the control unit 24 reads from the memory 26 the setting information associated with the newly determined situation. The setting information is the setting value associated with the focal position, whether or not to perform the inversion processing, whether or not to perform the illumination, the setting value of the magnification (angle of view), and the setting value of the depth of field.

The control unit 24 outputs a control signal based on the read setting information to the microscope 10.

In the microscope 10, the focal position of the transmission optical system 30, the inversion processing, the illumination, the magnification (angle of view), and the depth of field are controlled on the basis of the control signal output from the control device 20.

As shown in FIG. 7, the setting value (setting information) regarding the magnification (angle of view) in the situation of setting the insertion position of the surgical instrument and the situation in the middle of inserting the surgical instrument is a magnification of "a" to obtain a wide angle of view. In the situation of setting the insertion position of the surgical instrument and the situation in the middle of inserting the surgical instrument, it is favorable to obtain a wide angle of view with which the region outside the front lens 132 in which the trocar 50 is placed can also be observed in addition to the region of the front lens 132 in the captured image and the display image.

Based on this setting information, the control unit 24 controls the variable magnification lens system 172 of the observation optical system 17 to have the magnification of "a". The magnification of "a" is a preset setting value and is a default value determined with a generally-used value.

The setting value (setting information) regarding the depth of field in the situation of setting the insertion position of the surgical instrument and the situation in the middle of inserting the surgical instrument is a value at which the depth of field is deeper.

Based on this setting information, the control unit 24 controls the focusing device 171 and the variable aperture 173.

As shown in FIG. 7, the setting value (setting information) regarding the magnification (angle of view) in the situation in the middle of treatment is a magnification of "b" to have a narrow angle of view. In the middle of treatment, it is favorable to have a narrow angle of view to observe the region inside the front lens 132 in which the operative field is located.

Based on this setting information, the control unit 24 controls the variable magnification lens system 172 of the observation optical system 17 to have the magnification of "b". The magnification of "b" is a preset setting value and is a default value determined with a generally-used value. The magnification of "b" is a magnification higher than the magnification of "a".

The setting information regarding the depth of field in the situation in the middle of treatment can be set by the user. Based on the user's setting, the control unit 24 controls the focusing device 171 and the variable aperture 173.

It should be noted that in general, the depth of field is set to be shallower in the situation in the middle of treatment where the resolution and brightness are considered as important. Therefore, the setting value associated with the depth of field in the situation in the middle of treatment may be preset such that the depth of field is shallower. Then, the user may arbitrarily perform fine adjustment from a preset setting value.

As shown in FIG. 7, the setting information regarding the magnification (angle of view) in the situation in the middle of removing the surgical instrument is the magnification of "a" to obtain a wide angle of view. In the middle of removing the surgical instrument, it is favorable to obtain a wide angle of view such that the region outside the front lens 132 in which the trocar 50 is placed can also be observed in addition to the region inside the front lens 132 in the captured image and the display image in order to observe the area from the entire fundus to the trocar 50 for the sake of safe operation.

Based on this setting information, the control unit 24 controls the variable magnification lens system 172 of the observation optical system 17 to have the magnification of "a".

Moreover, the setting value (setting information) regarding the depth of field in the situation in the middle of removing the surgical instrument is a value at which the depth of field is deeper. Based on this setting information, the control unit 24 controls the focusing device 171 and the variable aperture 173.

Next, the operation of the control device 20 is described.

Figure 11:
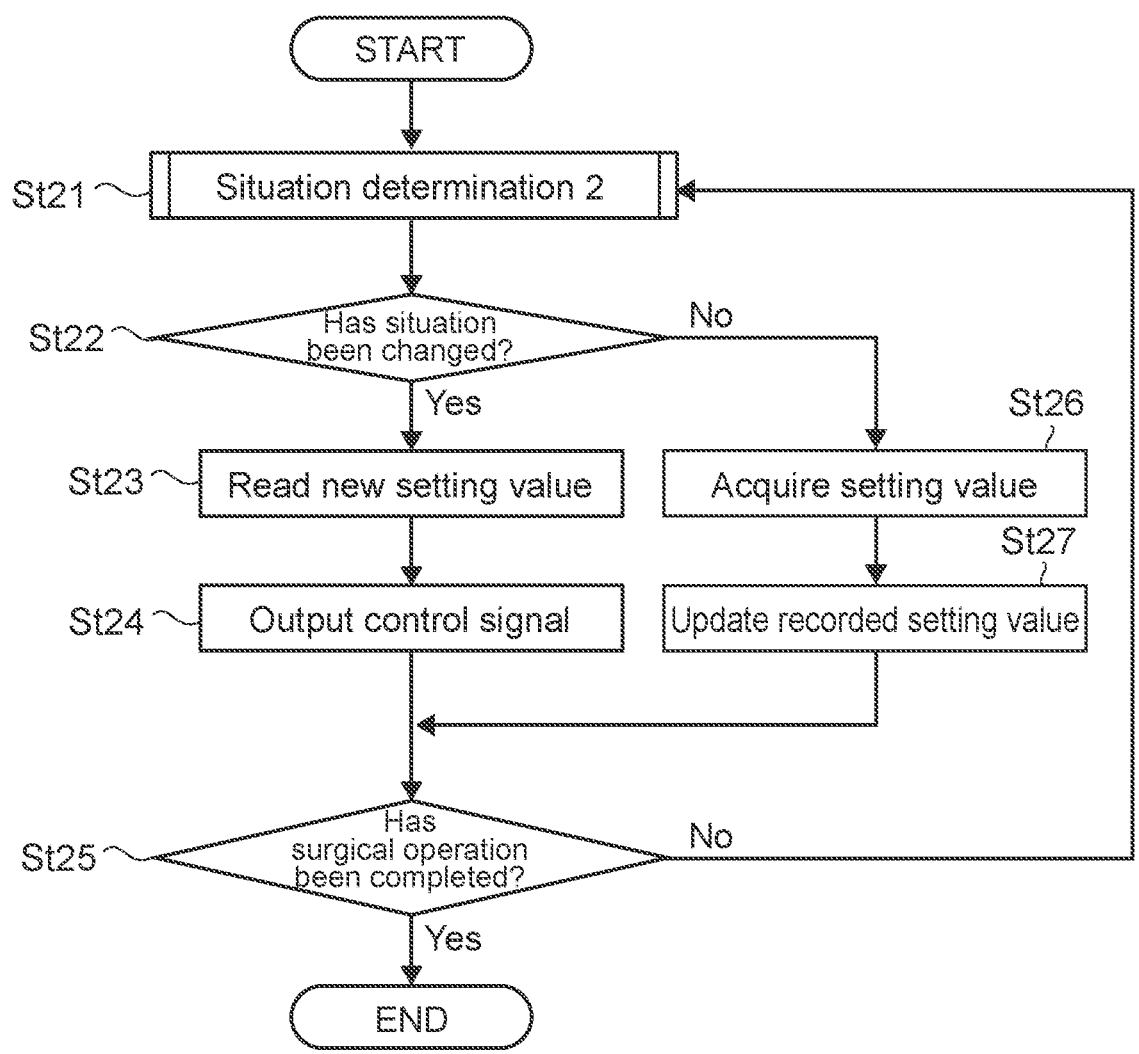
FIG. 11 A flowchart showing an operation of a control device according to a second embodiment.

FIG. 11 is a flowchart showing the operation of the control device 20 in a case where the insertion situation is divided into three situations: a situation in the middle of treatment; a situation in the middle of inserting the surgical instrument; and a situation in the middle of removing the surgical instrument, the three situations are determined, and the change of the setting value by the user's fine adjustment is recorded.

First, when the front lens 132 is placed on the observation optical path, the control unit 24 reads from the memory 26 preset setting information associated with the situation of setting the insertion position of the surgical instrument, which is shown in FIG. 7. The setting information includes the setting value associated with the focal position, whether or not to perform inversion processing, whether or not to perform the illumination, the magnification (angle of view), and the depth of field. Next, the control unit 24 outputs a control signal generated on the basis of the read setting information to the microscope 10.

In the microscope 10, the focal position of the transmission optical system 30 is controlled to be on the trocar 50 on the basis of the control signal output from the control device 20. Moreover, the inverted image correction inverter 14 is controlled not to perform the inversion processing. Moreover, the output of the illumination light from the intraocular illumination light source 191 and the microscope illumination light source 161 is controlled such that the extraocular illumination is present, the magnification is controlled to have the magnification of "a", and the depth of field is controlled to be deeper.

Figure 12:
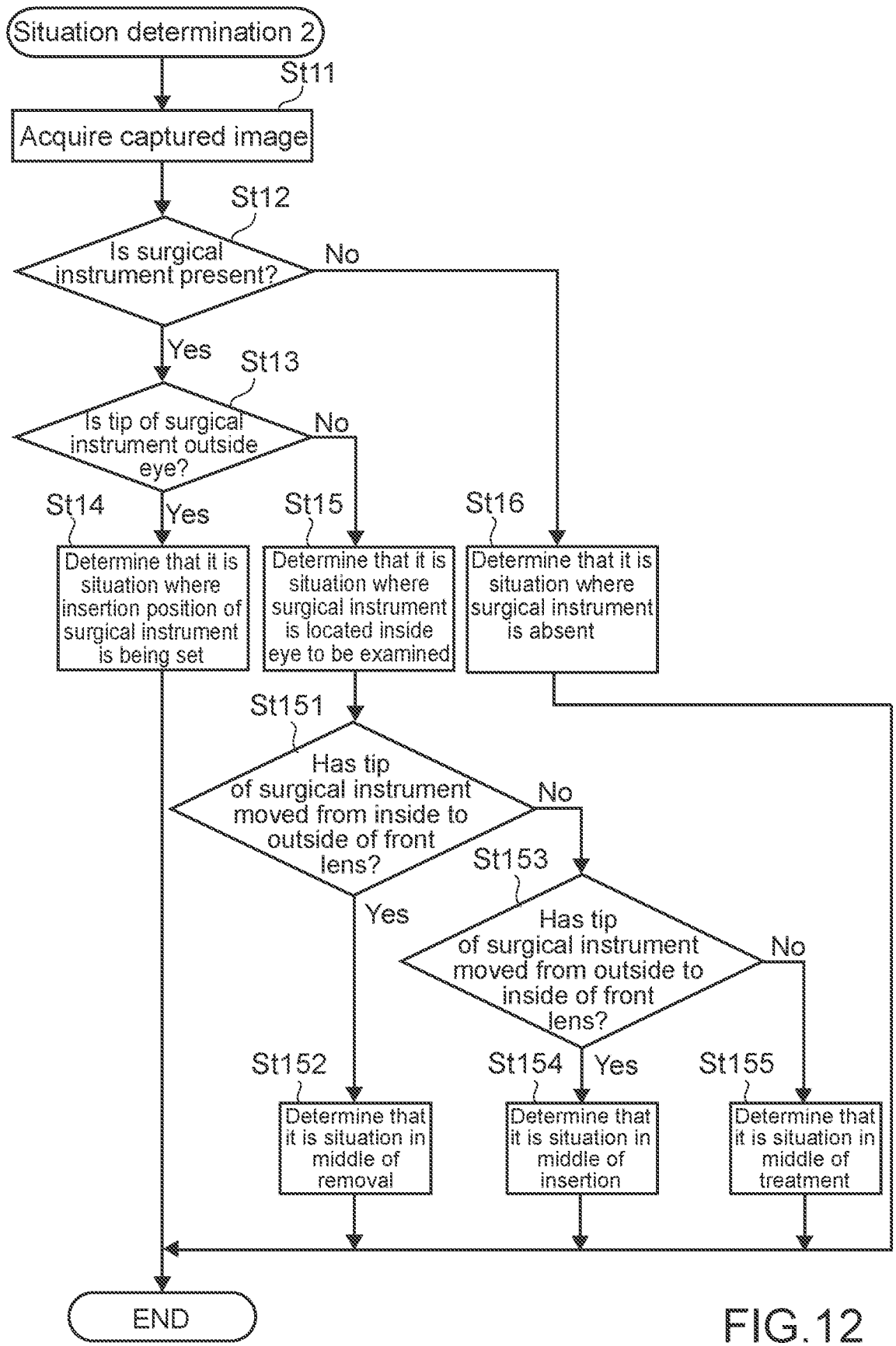
FIG. 12 A flowchart showing an operation of a situation determination 2 at St21 shown in FIG. 11.

Next, as shown in FIG. 11, the processing of a situation determination 2 is first performed (St21). FIG. 12 is a flowchart regarding the situation determination 2, the same steps as the processing of the situation determination 1 described in the first embodiment will be given the same step names, and descriptions thereof will be omitted. As shown in FIG. 12, in the situation determination 2, the situation where the surgical instrument is located inside the eye to be examined is further classified into three situations: a situation in the middle of insertion; a situation in the middle of treatment; and a situation in the middle of removal.

As shown in FIG. 12, in a case where it is determined in St15 that the surgical instrument is located inside the eye to be examined 6, the processing proceeds to St151.

In St151, the surgical instrument detection unit 22 detects whether or not the tip of the surgical instrument T is continuously moving from the inside to the outside in the region of the front lens 132 in the captured image.

In a case where it is detected that the tip of the surgical instrument T is moving from the inside to the outside (YES), the determination unit 23 determines that it is a situation where the surgical instrument T is being removed (St152).

In a case where it is detected that the tip of the surgical instrument T is not moving from the inside to the outside (NO), the processing proceeds to St153.

In St153, the surgical instrument detection unit 22 detects whether or not the tip of the surgical instrument T is continuously moving from the outside to the inside in the region of the front lens 132 in the captured images.

In a case where it is detected that the tip of the surgical instrument T is continuously moving from the outside to the inside (YES), the determination unit 23 determines that it is the situation in the middle of insertion (St154).

In a case where it is detected that the tip of the surgical instrument T is not continuously moving from the outside to the inside (NO), the determination unit 23 determines that it is the situation in the middle of treatment (St155).

As described above, the situation determination 2 (St21) is performed, and the processing proceeds to St22 below.

In St22, the determination unit 23 determines whether or not the determined situation has changed from the immediately preceding situation.

In St22, in a case where the determination unit 23 determines that the situation has not changed (NO), the control unit 24 acquires the setting information such as the setting value associated with the focal position, whether or not to perform the inversion processing, whether or not to perform the illumination, the setting value of the magnification, and the setting value associated with the depth of field at the current time (St26).

For example, the setting values of the focal position, the magnification, and the depth of field are changed by the user's fine adjustment, and the setting values recorded in advance as the default values may differ from the setting values at the current time in some cases. The resetting value (resetting information) adjusted and set by the user is acquired in St26.

The control unit 24 updates the recorded setting values reset and recorded so far to be the acquired resetting value (St27).

In St22, in a case where the determination unit 23 determines that the situation has changed (Yes), the control unit 24 reads the setting information (new setting information) according to the newly determined situation (St23). Here, in a case where the resetting value previously finely adjusted and set by the user is updated and recorded, the updated and stored recorded setting value is read in preference to the preset setting value (default value) as a new setting value.

The control unit 24 generates a control signal based on the read new setting value (new setting information) and outputs the control signal to the microscope 10 (St24).

In the microscope 10, the focal position, the inversion processing, the illumination, the magnification (angle of view), and the depth of field are controlled on the basis of the control signal output from the control device 20.

Next, it is determined whether or not the surgical operation has been completed (St25).

In a case where it is determined that the surgical operation has been completed (YES), the series of processing ends. In a case where it is determined that the surgery is not completed (NO), the processing returns to St21 and the processing is repeated.

In this manner, the memory 26 for recording the resetting information adjusted by the user of the microscope is provided and the control unit 24 controls the microscope 10 by using the resetting information in preference to the preset setting information in accordance with the determined situation, to thereby improve the work efficiency associated with the setting of the microscope 10.

That is, by updating and recording the resetting value adjusted by the user, it is possible to set the microscope 10 by using the resetting value updated under a similar situation thereafter, and it is unnecessary for the user to perform fine adjustment again, to thereby improve the work efficiency.

For example, a surgical instrument may be reinserted for performing treatment during a single same surgical operation. It is assumed that the user performs fine adjustment of the focal position and the like in treatment at the time of first insertion of the surgical instrument and a final setting value in the treatment, on which the fine adjustment has been reflected, is recorded. At the time of second or subsequent insertion of the surgical instrument, the microscope 10 can be controlled using the recorded setting value and the user can eliminate the labor of performing fine adjustment again.

It should be noted that a configuration may be made such that in a case where switching of the setting information due to the situation change is performed by the user's input operation through the foot switch or the like, the setting information is set to a resetting value on which the user's fine adjustment is reflected by operating the same switch as the switch used for the switching. Additionally, a switch for memory may be provided separately from the switch used for the switching.

Additionally, in the next other operation, the user may use a resetting value reflecting the user's fine adjustment, which has been used in the previous surgical operation, may use a default value, may use a setting value newly set by the user, or may be selectable by the user as appropriate.

As described above, the situation where the surgical instrument is inside the eye to be examined may be further divided into the three situations: the situation in the middle of treatment; the situation in the middle of inserting the surgical instrument; and the situation in the middle of removing the surgical instrument, the three situations are determined, and the magnification (angle of view) and the depth of field may be controlled in addition to the control of the focal position, the inversion processing, and the illumination in accordance with each situation.

Additionally, the resetting value reflecting the user's fine adjustment may be recorded and the control may be performed by using the updated resetting value.

Third Embodiment

In the above-mentioned embodiment, the example in which the inversion processing is performed by using the inverted image correction inverter 14 has been described, though not limited thereto. For example, the inversion processing may be performed by performing image processing on the captured image acquired by the image pickup element 181 and it will be described with reference to FIG. 13.

Figure 13A:
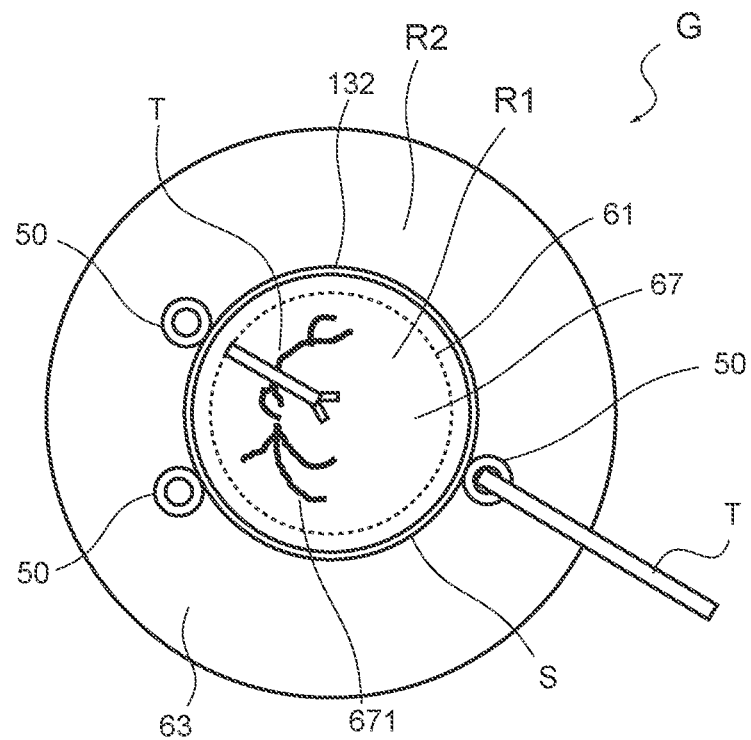
FIGS. 13A and 13B Diagrams for describing inversion processing in an ophthalmic microscope system according to a third embodiment.

FIG. 13A is a schematic diagram showing a captured image of an eye to be examined observed through the front lens 132 and the inversion processing by the inverted image correction inverter 14 is not performed.

Figure 13B:
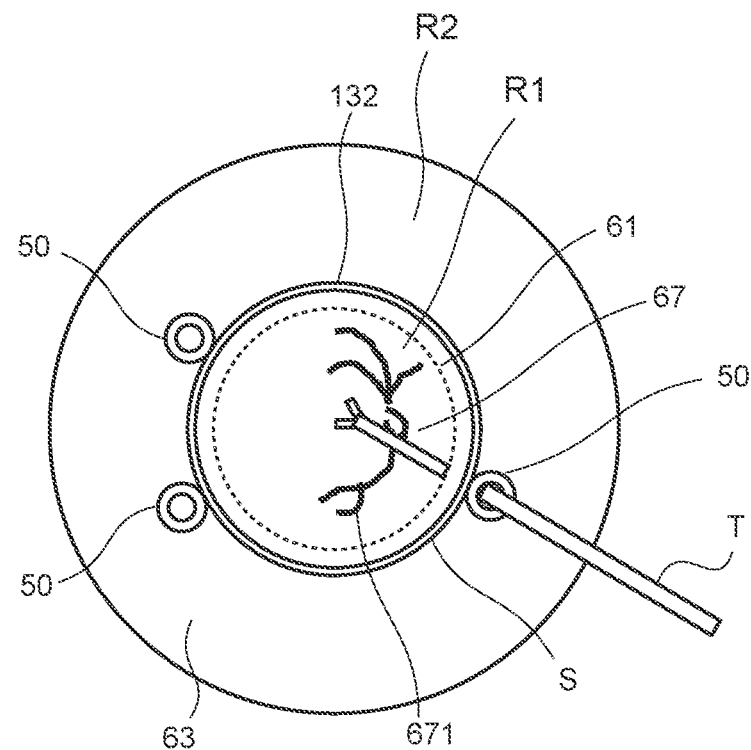

FIG. 13B is a schematic diagram showing a display image subjected to inversion processing by image processing.

As shown in FIG. 13A, in the captured image G, the front lens 132 is placed in front of the eye to be examined 6, such that a region inside a peripheral edge S of the front lens 132 becomes an inversion region R1 in which the image is inverted. The inversion region R1 is a region in which the image is formed by the front lens 132. In FIGS. 13A and 13B, the region in which the image is not inverted is shown as a non-inversion region R2.

Detection of the inversion region R1 in the captured image is performed by an inversion region detection unit (not shown) provided in the control device 20.

In addition to generating a control signal for controlling the microscope 10 described in the above-mentioned embodiment, the control unit 24 of the control device 20 causes the inversion region detection unit to detect the inversion region and the image processing unit 25 to perform the inversion processing of the captured image in a case where it is a situation where the setting information indicates that the inversion processing is to be done.

Detection of the inversion region R1 can be performed using object recognition. Alternatively, the inversion region R1 may be detected by using the fact that the outside of the front lens 132 is a region (white 63 of the eye) corresponding to a sclera while the inside of the front lens 132 is a region (cornea) having color and texture different from those of the white of the eye, such as an iris and a pupil.

Alternatively, it is also possible to perform edge detection processing and detect the region inside the detected edge as the inversion region R1 because there is a clear edge at the peripheral edge S of the front lens 132 in the captured image.

The above-mentioned detection methods detect the inversion region R1 from the single captured image.

Moreover, in a case where the image pickup element 181 is mounted on each of the right and left sides of the microscope 10, captured images for both the left eye and the right eye can be obtained. Depth information may be extracted from parallax information of the two captured images and the inversion region R1 may be detected by using the fact that the front lens 132 is placed in front of the eye.

Alternatively, the inversion region R1 may be detected using a plurality of captured images. Specifically, a captured image when the front lens 132 is not mounted may be retained, the captured image may be compared with a captured image including the front lens 132, and a region having a large difference therebetween may be detected as the inversion region R1.

The range of the detected inversion region R1 is supplied to the image processing unit 25.

In a case where the setting information indicates that the inversion processing is to be done, the image processing unit 25 inverts the inversion region R1 included in the captured image output from the image pickup element 181 to be point-symmetric about the center of the inversion region R1. In addition, the image processing unit 25 combines the inversion region R1 and the non-inversion region R2 by matching the outer periphery of the inverted inversion region R1 and the inner periphery of the non-inversion region R2.

Accordingly, the image processing unit 25 is capable of generating a display image in which the inversion is cancelled as shown in FIG. 13B. The image processing unit 25 outputs the generated display image to the display device 40 for displaying the generated display image on the display device 40.

As described above, the inversion processing may be performed by the image processing to generate the display image, and the user can insert or remove the surgical instrument T and perform treatment of the eye to be examined 6 while viewing the display image displayed on the display device 40.

Fourth Embodiment

A description will be given of an ophthalmic microscope system (hereinafter, referred to as microscope system) 400 according to a fourth embodiment. Here, retinal vitreous surgery using a wide-angle observation lens as a front lens will be described as an example.

The microscope system 400 according to this embodiment is an HUS system that performs a surgical operation while viewing an image captured by an image pickup element on a display device. Configurations similar to those in the above-mentioned embodiments will be denoted by similar reference signs and descriptions thereof will be omitted in some cases. It should be noted that in this embodiment, a configuration is made such that the eyepiece lens unit is not provided and the eye to be examined is observed through the display device, though a configuration may be made such that the eyepiece lens unit is provided as in the first embodiment and both the observation through the eyepiece and the observation through the display device can be performed.
[Configuration of Ophthalmic Microscope System]

Figure 14:
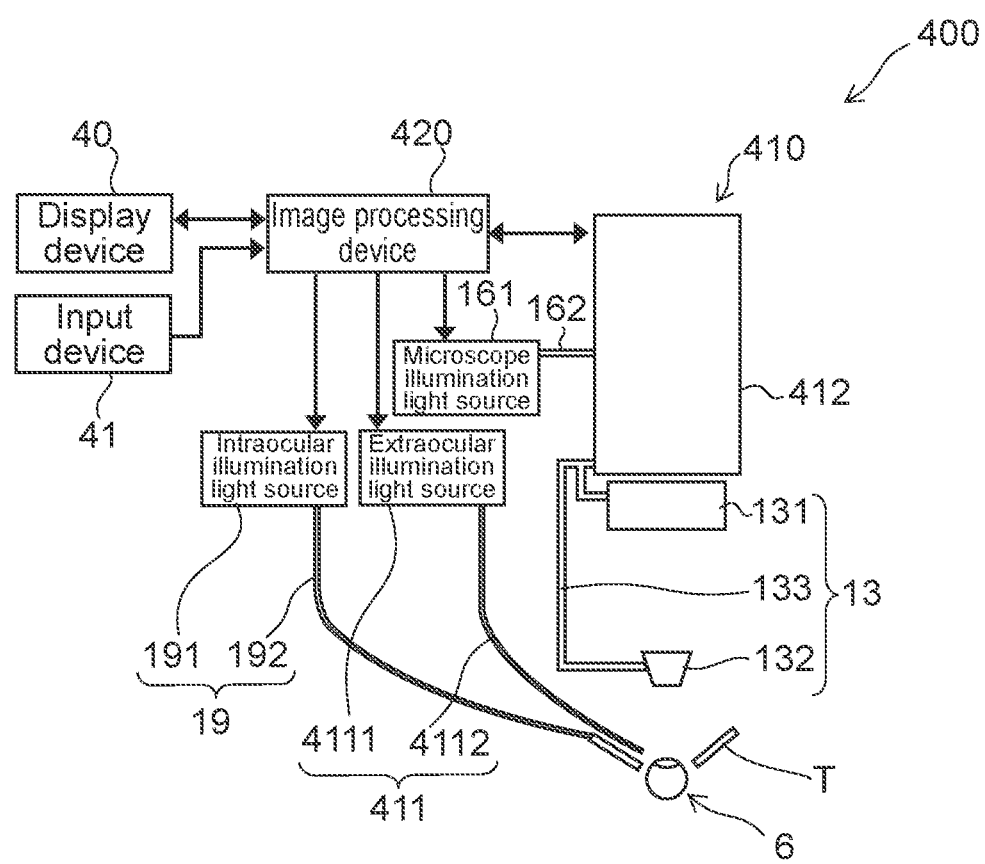
FIG. 14 A schematic diagram of an ophthalmic microscope system according to a fourth embodiment.

FIG. 14 is a schematic diagram showing a configuration of the microscope system 400 according to this embodiment.

As shown in FIG. 14, the microscope system 400 includes an ophthalmic microscope (hereinafter, referred to as microscope) 410, an image processing device 420, a display device 40, and an input device 41.

Although the details will be described later, the microscope 410 includes an intraocular observation image pickup element 4181 serving as a first image pickup element for imaging the eye to be examined 6, in front of which a front lens 132 is placed, by focusing on the front lens 132 and an extraocular observation image pickup element 4182 serving as a second image pickup element for performing imaging by focusing on a region of the eye to be examined 6, in front of which the front lens 132 is not placed.

The display device 40 displays a display image generated using a first captured image acquired by the intraocular observation image pickup element 4181 and a second captured image acquired by the extraocular observation image pickup element 4182.

The display image is generated by combining a first image obtained by extracting a region in the first captured image, in which the front lens 132 is located, and inverting only the extracted region, and a second image formed by a region other than a region in the second captured image, in which the front lens 132 is located.

The details thereof will be described below.

The microscope 410 is used by a user of the microscope system 400 (ophthalmologist who examines the eye to be examined by using the microscope system 400, a surgeon who performs a surgical operation by using the microscope system 400, an assistant, or the like) to observe a magnified image of the eye to be examined 6 in examination or surgery in the ophthalmologic field.

As shown in FIG. 14, the microscope 410 includes a microscope body 412, a contactless wide-angle observation unit 13 serving as a function expansion unit, an intraocular illuminator 19, a microscope illumination light source 161, and an extraocular illuminator 411. The details of the microscope 410 will be described later.

The image processing device 420 performs image processing on an image captured by the intraocular observation image pickup element 4181 and the extraocular observation image pickup element 4182, which have been mounted on the microscope 410 and will be described later, and generates a display image to be displayed on the display device 40. The details of the image processing device 420 will be described later.

The display device 40 displays the display image generated by the image processing device 420.

The input device 41 is an input interface to the microscope system 400 and is similar to that of the first embodiment.
[Configuration of Microscope]

Next, the microscope 410 will be described.

Figure 15:
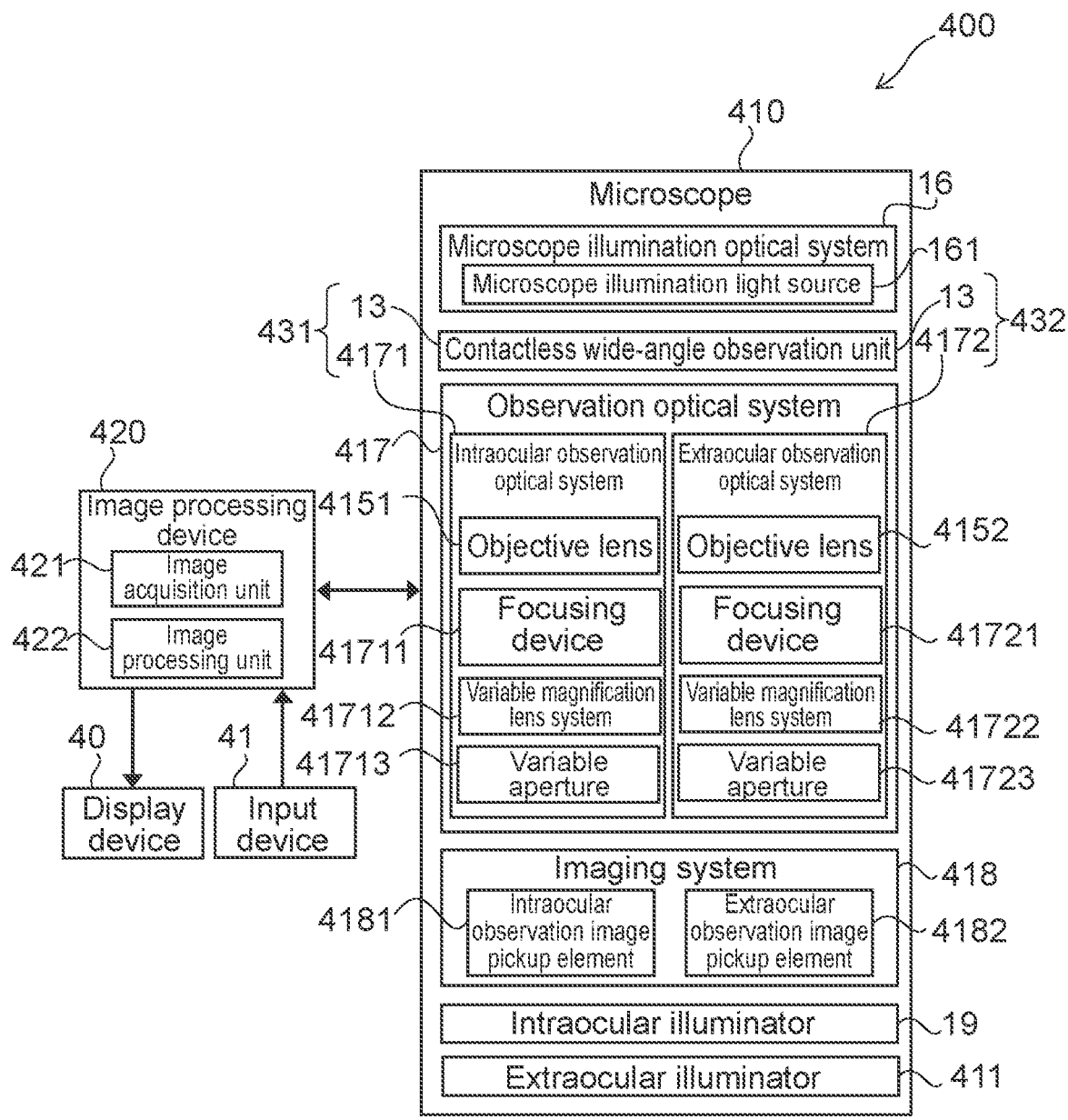
FIG. 15 A block diagram of the ophthalmic microscope system of FIG. 14.

FIG. 15 is a block diagram of the microscope system 400.

As shown in FIG. 15, the microscope 410 includes the contactless wide-angle observation unit 13, a microscope illumination optical system 16, an observation optical system 417, an imaging system 418, the intraocular illuminator 19, and the extraocular illuminator 411.

The microscope body 412 houses a part of the microscope illumination optical system 16, the observation optical system 417, and the imaging system 418.

The configurations of the contactless wide-angle observation unit 13, the microscope illumination optical system 16, and the intraocular illuminator 19 are similar to those of the first embodiment.

Figure 16:
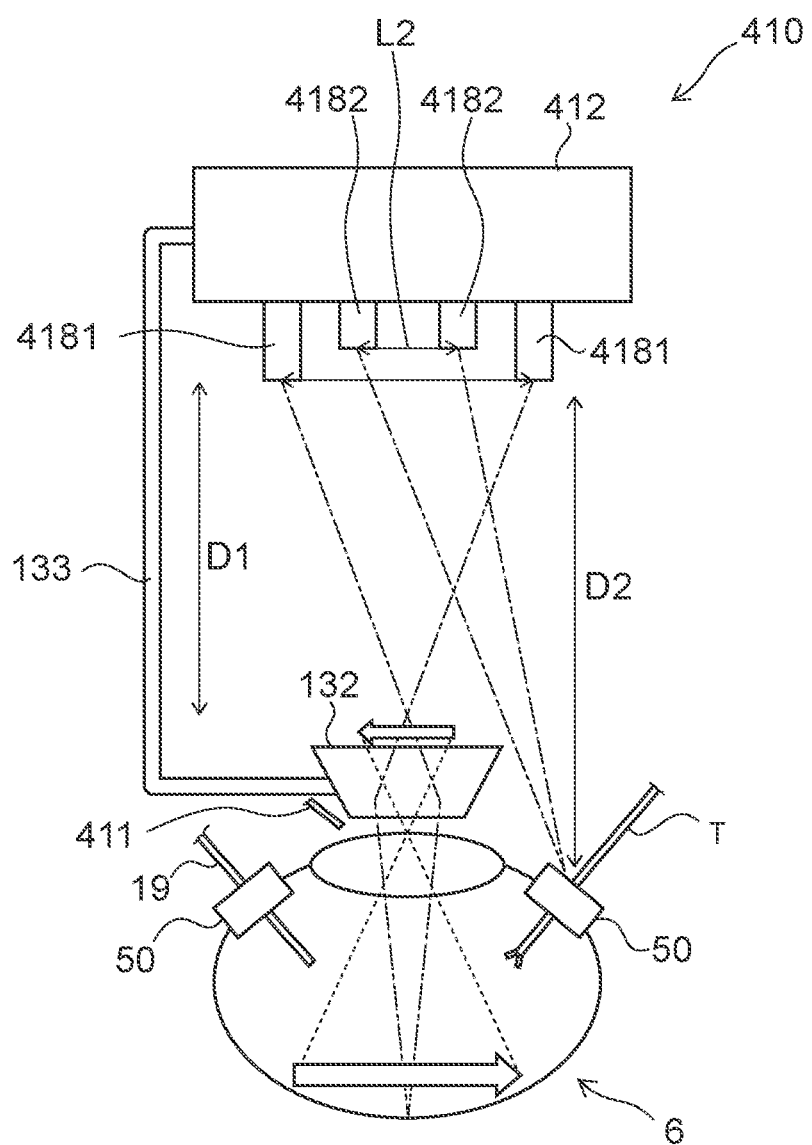
FIG. 16 A schematic diagram showing a state of the surgery of the eye using the ophthalmic microscope system of FIG. 14.

FIG. 16 is a schematic diagram for describing a state of the eye surgery using the microscope system 400. In FIG. 16, the illustration of the reduction lens 131 is omitted.

As shown in FIGS. 14 and 16, the extraocular illuminator 411 is provided outside the microscope body 412 and is for emitting illumination light for illuminating the eye to be examined 6 from the outside of the eye to be examined 6. The extraocular illuminator 411 is provided in the contactless wide-angle observation unit 13, for example.

As shown in FIG. 14, the extraocular illuminator 411 includes an extraocular illumination light source 4111 and an optical fiber 4112.

The extraocular illumination light source 4111 emits illumination light (extraocular illumination light). One end of the optical fiber 4112 is connected to the extraocular illumination light source 4111 and the other end of the optical fiber 4112 is placed to be located on the side of the front lens 132 as shown in FIG. 16.

As shown in FIG. 16, when the front lens 132 is placed in front of the eye to be examined 6, the illumination light from the microscope illumination optical system 16 illuminates the eye to be examined 6 via the front lens 132. On the other hand, the illumination light from the extraocular illuminator 411 illuminates the eye to be examined 6 not via the front lens 132.

The extraocular illuminator 411 serving as the extraocular illumination optical system and the microscope illumination optical system 16 both output extraocular illumination light for illuminating the eye to be examined 6 from the outside. However, since the illumination light from the extraocular illuminator 411 illuminates the eye to be examined 6 not via the front lens 132, the illumination light is not reflected on the front lens 132.

Whether or not to output the illumination light from the microscope illumination light source 161, whether or not to output the illumination light from the intraocular illumination light source 191, and whether or not to output the illumination light from the extraocular illumination light source 4111 may be controlled by the user's input operation. Additionally, control may be performed on the basis of setting information preset in accordance with a situation determined by using the surgical instrument detection result of the captured image as in the above-mentioned embodiment.

The observation optical system 417 is for observing the eye to be examined 6 illuminated by the microscope illumination optical system 16, the intraocular illuminator 19, or the extraocular illuminator 411.

The observation optical system 417 includes an intraocular observation optical system 4171 serving as a first observation optical system and an extraocular observation optical system 4172 serving as a second observation optical system.

The intraocular observation optical system 4171 is provided with an observation optical path in association with the intraocular observation image pickup element 4181 and the extraocular observation optical system 4172 is provided with an observation optical path in association with the extraocular observation image pickup element 4182.

The contactless wide-angle observation unit 13 and the intraocular observation optical system 4171 (extraocular observation optical system 4172) constitute an intraocular transmission optical system 431 (extraocular transmission optical system 432) as a first optical system (second optical system) for transmitting an image of the eye to be examined 6 to the intraocular observation image pickup element 4181 (extraocular observation image pickup element 4182).

The intraocular transmission optical system 431 (extraocular transmission optical system 432) is an optical system that forms an image of return light (the image of the eye to be examined) from the eye to be examined 6 on the intraocular observation image pickup element 4181 (extraocular observation image pickup element 4182).

More specifically, the intraocular transmission optical system 431 is constituted by the front lens 132, the reduction lens 131, and the intraocular observation optical system 4171.

The extraocular transmission optical system 432 is constituted by the reduction lens 131 and the extraocular observation optical system 4172.

The intraocular observation optical system 4171 and the extraocular observation optical system 4172 are each divided into an observation optical system for the left eye and an observation optical system for the user's right eye and each have an observation optical path. Unless it is particularly necessary to distinguish between the one for the right eye and the one for the left eye, the observation optical systems will be referred to as the intraocular observation optical system 4171 and the extraocular observation optical system 4172.

The intraocular observation optical system 4171 (extraocular observation optical system 4172) includes an objective lens 4151 (4152), a focusing device 41711 (41721), a variable magnification lens system 41712 (41722) including a plurality of zoom lenses, an imaging lens (not shown), a variable aperture 41713 (41723), and an imaging lens (not shown).

The focusing device 41711 (41721) is capable of moving the intraocular observation optical system 4171 (extraocular observation optical system 4172) up and down. Accordingly, it is possible to adjust the operation interval between the objective lens 4151 (4152) and the eye to be examined 6 of the patient and the microscope 410 is focused on a region to be examined of the eye to be examined 6.

It should be noted that in this embodiment, the focusing device 41711 and the focusing device 41712 are configured to be each independently controllable. The focal position, the magnification, and the depth of field of the transmission optical system are individually controlled by the intraocular transmission optical system 431 and the extraocular transmission optical system 432.

In this embodiment, the focusing device 41711 of the intraocular observation optical system 4171 adjusts a distance D1 from the front lens 132 to the object-side principal point of the objective lens 4151 to focus on the region in which the front lens 132 is located in a state in which the front lens 132 is placed in front of the eye to be examined 6.

In this manner, the focal position of the intraocular transmission optical system 431 is set to be located in the region in which the front lens 132 is located.

The state in which the focal position of the intraocular transmission optical system 431 is located in the region in which the front lens 132 is located is as follows. That is, the relative positional relationship among the objective lens 4151, the front lens 132, and the eye to be examined 6 is adjusted such that the position of the back focal point of the front lens 132 coincides with the position of the front focal point of the objective lens 4151 and the fundus 67 is focused.

Moreover, a distance D2 from the object-side principal point of the objective lens 4152 to a trocar 50 placed on the eye to be examined 6 is adjusted by the focusing device 41721 of the extraocular observation optical system 4172 to focus on the trocar 50 located outside the front lens 132 in a state in which the front lens 132 is placed in front of the eye to be examined 6. It should be noted that in a case where the trocar 50 is not used, the distance from the object-side principal point of the objective lens 4152 to the surface of the eye to be examined 6 is defined as D2.

Thus, the focal position of the extraocular transmission optical system 432 is set to be located on a region outside the region in which the front lens 132 is located, more particularly, the trocar 50. The state in which the focal position of the extraocular transmission optical system 432 is located on the trocar 50 is a state in which the front focal position of the objective lens 4152 is set to be located on the trocar 50.

The plurality of zoom lenses of the variable magnification lens system 41712 (41722) is movable along the optical axis of the observation optical system. The movement of the plurality of zoom lenses changes the magnification for imaging the eye to be examined 6.

The depth of field of the intraocular transmission optical system 431 and the extraocular transmission optical system 432 depends on the focal length of the lens, the F-value, and the imaging distance. Therefore, the depth of field is changed by controlling the focusing device 41711 (41721) and the variable aperture 41713 (41723).

The return light reflected and scattered by the eye to be examined 6 and entering the objective lens 4151 (4152) has the magnification controlled by the variable magnification lens system 41712 (41722), passes through the imaging lens and the variable aperture 41713 (41723), enters the imaging lens, and enters the intraocular observation image pickup element 4181 (extraocular observation image pickup element 4182) of the imaging system 418, which will be described later.

The imaging system 418 includes the intraocular observation image pickup element 4181 and the extraocular observation image pickup element 4182.

The intraocular observation image pickup element 4181 (extraocular observation image pickup element 4182) may correspond to both the left and right intraocular observation optical systems 4171 (extraocular observation optical systems 4172) or may correspond to one of the left and right intraocular observation optical systems 4171 (extraocular observation optical systems 4172). In this embodiment, the intraocular observation image pickup element 4181 (extraocular observation image pickup element 4182) corresponds to both the left and right ones, and two intraocular observation image pickup elements 4181 (extraocular observation image pickup elements 4182) are shown in the example shown in FIG. 16. Thus, it is possible to obtain a stereo image since the image pickup elements are provided for the left and right in this embodiment.

The intraocular observation image pickup element 4181 and the extraocular observation image pickup element 4182 are mounted on the microscope 410. The image of the eye to be examined 6 is formed on the intraocular observation image pickup element 4181 (extraocular observation image pickup element 4182) via the intraocular transmission optical system 431 (extraocular transmission optical system 432). The captured image captured by the intraocular observation image pickup element 4181 and the extraocular observation image pickup element 4182 is output to the image processing device 420.

As shown in FIG. 16, the intraocular observation image pickup element 4181 is placed to image the eye to be examined 6 through the front lens 132.

The distance D1 between the object-side principal point of the objective lens 4151 and the front lens 132 is adjusted such that the focal position of the intraocular transmission optical system 431 associated with the intraocular observation image pickup element 4181 falls within the region in which the front lens 132 is located as the eye to be examined 6 is viewed from the front side. The first captured image captured by the intraocular observation image pickup element 4181 is an image focused on the front lens 132 as the eye to be examined 6 is viewed from the front side.

On the other hand, as shown in FIG. 16, the extraocular observation image pickup element 4182 is placed to image the eye to be examined 6 not via the front lens 132 in a state in which the front lens 132 is placed in front of the eye to be examined 6.

The distance D2 between the object-side principal point of the objective lens 4152 and the trocar 50 is adjusted such that the focal position of the extraocular transmission optical system 432 associated with the extraocular observation image pickup element 4182 is on the trocar 50 located outside the region in which the front lens 132 is located as the eye to be examined 6 is viewed from the front side. The second captured image acquired by the extraocular observation image pickup element 4182 becomes an image focused on the region outside the front lens 132

By using the intraocular observation image pickup element 4181 and the extraocular observation image pickup element 4182 as described above, it is possible to obtain captured images having different focal positions in the respective image pickup elements.

[Configuration of Image Processing Device]

Next, the image processing device 420 will be described. The image processing device 420 generates a display image on the basis of the first captured image and the second captured image acquired from the microscope 410. It should be noted that in this embodiment, the inversion processing is performed by the image processing without using the inverted image correction inverter.

As shown in FIG. 15, the image processing device 420 includes an image acquisition unit 421 and an image processing unit 422.

The image acquisition unit 421 acquires the first captured image captured by the intraocular observation image pickup element 4181 and the second captured image captured by the extraocular observation image pickup element 4182.

The image processing unit 422 extracts an inversion region in which the front lens 132 is located in the first captured image (the region in which the image is inverted by the front lens 132) and inverts only the extracted region as a normal image, to thereby generate the first image. In addition, the image processing unit 422 generates the second image obtained by extracting a region of the second captured image, which is other than the region in which the front lens 132 is located. Then, the first image and the second image are combined to generate a display image. The generated display image is output to the display device 40.

The display device 40 displays the display image, and the user can observe the eye to be examined 6 while viewing the displayed display image.

The inversion processing of the inversion region of the first captured image is similar to that of the third embodiment.

Thus, in this embodiment, the display image generated by combination is an image focused on each of the region in which the front lens 132 is present and the region in which the front lens 132 is absent, and is a display image with which the inside and outside of the front lens 132 can be naturally observed. Therefore, the user can observe each region simultaneously with an appropriate image.

Moreover, in the microscope system 400 according to this embodiment, it is unnecessary to control the microscope to change the focal position for changing from the situation where the insertion position of the surgical instrument T is to be set to the situation where the surgical instrument T is located inside the eye to be examined 6, as compared to a case where the regions inside and outside the front lens 132 are captured by the same image pickup element. Therefore, the user is not bothered with the setting of the microscope.

Moreover, in this embodiment, since the extraocular illuminator 411 is placed on the side of the front lens 132, the illumination light can be radiated to the eye to be examined 6 not via the front lens 132.

In a case where the front lens 132 is placed in front of the eye to be examined 6, a display image suitable for observation without specular reflection of the illumination light on the front lens 132 can be obtained by irradiating the eye to be examined 6 with the illumination light from the extraocular illuminator 411, not the illumination light from the microscope illumination light source 161 as the extraocular illumination light.

In this embodiment, the extraocular illuminator 411 is provided on the side of the front lens 132 to thereby prevent the specular reflection on the front lens 132, though not limited thereto.

For example, a configuration is made such that the extraocular illuminator 411 is not provided as the extraocular illumination light for irradiating the eye to be examined 6 from the outside, and the illumination light from the microscope illumination optical system 16 is used. Then, imaging by the intraocular observation image pickup element 4181 and the extraocular observation image pickup element 4182 is alternately performed. In addition, the illumination light from the microscope illumination optical system 16 is blinked at a high speed at the time of imaging such that the radiation of the illumination light from the microscope illumination optical system 16 is turned off (extinguished) at the time of imaging with the intraocular observation image pickup element 4181 that performs imaging by focusing on the front lens 132, and that the radiation of illumination light from the microscope illumination optical system 16 is turned on (lit) at the time of imaging with the extraocular observation image pickup element 4182 that performs imaging by focusing on the outside of the front lens 132. It should be noted that the illumination light from the intraocular illuminator 19 is turned on at the time of imaging with the intraocular observation image pickup element 4181 and is turned off at the time of imaging with the extraocular observation image pickup element 4182.

Thus, in imaging in the front lens 132, the illumination light from the microscope illumination optical system 16 is not reflected on the front lens 132, and an image suitable for observation without specular reflection of the illumination light on the front lens 132 can be obtained.

Moreover, as another example, a configuration is made such that the extraocular illuminator 411 is not provided as the extraocular illumination light for irradiating the eye to be examined 6 from the outside and the illumination light from the microscope illumination optical system 16 is used. A configuration is made such that first illumination light output from the intraocular illuminator 19 has a first wavelength and second illumination light output from the microscope illumination optical system 16 has a second wavelength different from the first wavelength. In addition, the intraocular observation image pickup element 4181 serving as the first image pickup element is set as an image pickup element that selectively receives light having the first wavelength and the extraocular observation image pickup element 4182 serving as the second image pickup element is an image pickup element that selectively receives light having the second wavelength.

As a specific example, the intraocular illuminator 19 with which the illumination light (first illumination light) output from the intraocular illuminator 19 becomes illumination light (light having the first wavelength) from which near-infrared light has been cut off is used and the microscope illumination optical system 16 with which the microscope illumination light (second illumination light) output from the microscope illumination optical system 16 is near-infrared light (light having the second wavelength) is used. In addition, the intraocular observation image pickup element 4181 that selectively receives the light (light having the first wavelength) from which the near infrared light has been cut off is used and the extraocular observation image pickup element 4182 that selectively receives the near-infrared light (light having the second wavelength) is used.

Here, it is assumed that the illumination light is simultaneously radiated from the intraocular illuminator 19 and the microscope illumination optical system 16 and imaging is simultaneously by the intraocular observation image pickup element 4181 and the extraocular observation image pickup element 4182. In this case, even if the illumination light (near-infrared light) from the microscope illumination optical system 16 is reflected on the front lens 132 and enters the intraocular observation image pickup element 4181, the near-infrared light is not received by the intraocular observation image pickup element 4181 because the intraocular observation image pickup element 4181 receives the light from which the near-infrared light has been cut. Therefore, it is possible to obtain a captured image without the influence of the specular reflection of the illumination light at the front lens 132, and it is possible to obtain an image suitable for observation.

In addition, as another example, a configuration in which the extraocular illuminator 411 is not provided as the extraocular illumination light for irradiating the eye to be examined 6 from the outside and the illumination light from the microscope illumination optical system 16 is used. Then, the microscope illumination optical system 16 is configured such that the second illumination light from the microscope illumination optical system 16 has a particular polarization state (second polarization state). In addition, a polarizing filter serving as an optical element that allows only light in a first polarization state, which is orthogonal to the polarization state (second polarization state) of the second illumination light, from the microscope illumination optical system 16 to pass therethrough is provided in front of the intraocular observation image pickup element 4181.

Here, it is assumed that the illumination light is simultaneously radiated from the intraocular illuminator 19 and the microscope illumination optical system 16 and imaging is simultaneously performed by the intraocular observation image pickup element 4181 and the extraocular observation image pickup element 4182. In this case, when the illumination light in the particular polarization state from the microscope illumination optical system 16 is reflected on the front lens 132, the reflected light becomes light with the particular polarization state maintained. Therefore, the reflected light cannot pass through the polarizing filter provided in front of the intraocular observation image pickup element 4181 and does not enter the intraocular observation image pickup element 4181. Therefore, it is possible to obtain a captured image without the influence of the specular reflection of the illumination light on the front lens 132, and it is possible to obtain an image suitable for observation.

In general, a wide-angle observation lens capable of obtaining a wide-angle field of view is used as a front lens for fundus observation. The image obtained via the front lens is smaller as compared to the image obtained not via the front lens. Therefore, in an image obtained by combining the first image generated on the basis of the first captured image acquired by the intraocular observation image pickup element 4181 and the second image generated on the basis of the second captured image acquired by the extraocular observation image pickup element 4182, the sense of depth may greatly differ between the inside and the outside of the front lens.

On the other hand, since the intraocular observation image pickup element 4181 and the extraocular observation image pickup element 4182 are provided in the microscope system 400 according to this embodiment, it is possible to arrange the image pickup elements by adjusting the distance (base line length L2, see FIG. 16) between the extraocular observation image pickup element 4182 for the left eye and the extraocular observation image pickup element 4182 for the right eye. By changing the base line length L2, the size of the image acquired by the intraocular observation image pickup element 4181 can be adjusted.

Specifically, reducing the base line length L2 can enlarge the image in the front lens, which can make adjustment to provide a display image whose sense of depth is closer between the inside and the outside of the front lens.

Moreover, in the microscope system 400 according to this embodiment, the intraocular observation optical system 4171 and the extraocular observation optical system 4172 are provided associated with the intraocular observation image pickup element 4181 and the extraocular observation image pickup element 4182, respectively. Therefore, the focal position can be separately adjusted by the respective optical systems of the intraocular transmission optical system 431 including the intraocular observation optical system 4171 and the extraocular transmission optical system 432 including the extraocular observation optical system 4172. Thus, changing the distance D2 from the object-side principal point of the objective lens 4152 to the trocar 50 placed on the eye to be examined 6 can adjust the size of the image acquired by the intraocular observation image pickup element 4181.

Specifically, increasing the distance D2 can enlarge the image in the front lens, which can make adjustment to provide a display image whose sense of depth is closer between the inside and the outside of the front lens.

For adjusting the sense of depth between the inside and the outside of the front lens, either one of the base line length L2 and the distance D2 may be used or both the base line length L2 and the distance D2 may be used.

As described above, the microscope system according to this embodiment can assist the setting work of the microscope, and the user can observe the eye to be examined with an appropriate display image without being bothered with the setting of the microscope.

The embodiment of the present technology is not limited to the embodiments described above, and various modifications can be made without departing from the essence of the present technology.

Although the wide-angle observation lens is taken as an example of the front lens 132 in each of the above-mentioned embodiments, for example, a gonioscope may be used as the front lens 132, for example. The angle can be observed by using the gonioscope. In a case of the gonioscopy, the intraocular illumination becomes unnecessary. Thus, for example, the setting information regarding the illumination in the first embodiment is either on or off of the extraocular illumination in the microscope illumination optical system.

Although the example in which the situation where the surgical instrument is located inside the eye to be examined is divided into the three situations: the treatment situation; the situation in the middle of insertion; and the situation in the middle of removal and the three situations are determined has been given in the above-mentioned second embodiment, the situation where the surgical instrument is located inside the eye to be examined may be divided into a situation in the middle of treatment and a situation not in the middle of treatment, for example. Hereinafter, the description will be given with reference to FIG. 17.

Figure 17:
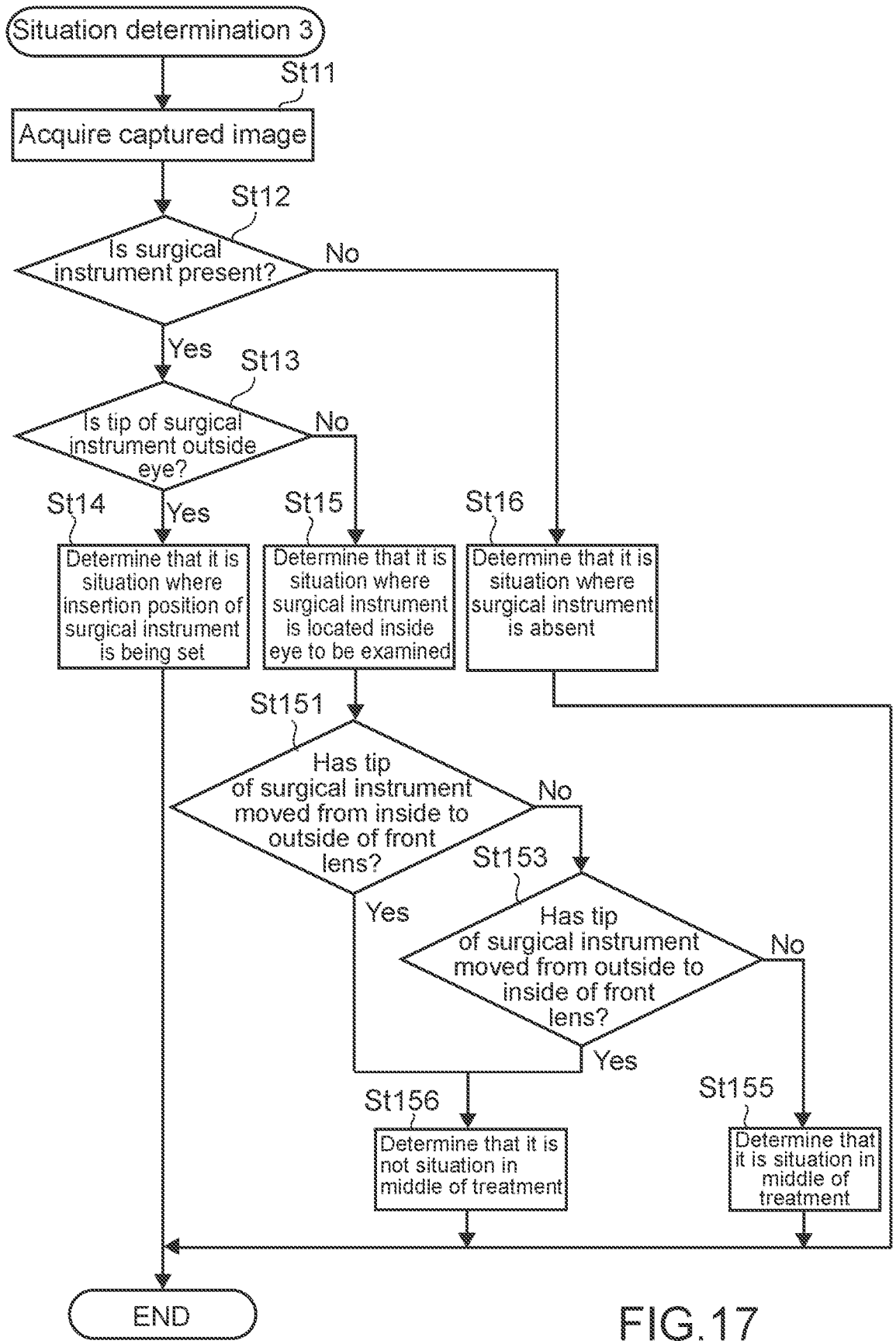
FIG. 17 A flowchart showing an operation of another situation determination.

FIG. 17 is a flowchart showing the operation of the control device 20 in a case where the situation where the surgical instrument is located inside the eye to be examined is divided into two situations: a situation in the middle of treatment; and a situation not in the middle of treatment and the two situations are determined. In FIG. 17, this situation determination is referred to as a situation determination 3. In FIG. 17, the same steps as those described in the above-mentioned embodiments will be given the same step names and descriptions thereof will be omitted in some cases.

As shown in FIG. 17, in St151, the surgical instrument detection unit 22 detects whether or not the tip of the surgical instrument T is continuously moving from the inside to the outside in the region of the front lens 132 in the captured image. In a case where it is detected that the tip of the surgical instrument T is moving from the inside to the outside (YES), the determination unit 23 determines that it is the situation not in the middle of treatment (St156). In a case where it is detected that the tip of the surgical instrument T is not being moving from the inside to the outside (NO), the processing proceeds to St153.

In St153, the surgical instrument detection unit 22 detects whether or not the tip of the surgical instrument T is continuously moving from the outside to the inside in the region of the front lens 132 in the captured image.

In a case where it is detected that the tip of the surgical instrument T is continuously moving from the outside to the inside (YES), the determination unit 23 determines that it is the situation not in the middle of treatment (St156).

In a case where it is detected that the tip of the surgical instrument T is not continuously moving from the outside to the inside (NO), the determination unit 23 determines that it is the situation in the middle of treatment (St155).

In this manner, the situation determination 3 is performed.

As described above, whether it is the situation in the middle of treatment or it is the situation not in the middle of treatment can be determined by using the surgical instrument detection result. The imaging condition of the image pickup element 181 can be automatically set on the basis of the magnification (angle of view) preset for each determination, the setting information associated with the depth of field.

In the example shown here, in a case where it is determined that it is the situation in the middle of treatment as shown in FIG. 7, the magnification is set to the magnification of "b" and the microscope 10 is controlled such that the depth of field can be set by the user. On the other hand, in a case where it is determined that it is the situation not in the middle of treatment, the magnification is set to the magnification of "a" and the microscope 10 is controlled such that the depth of field is deeper.

Here, the example in which both the magnification (angle of view) and the depth of field are automatically set has been shown, though either one of them may be automatically set. As described above, at least one of the magnification (angle of view) or the depth of field may be automatically controlled in accordance with the determination result of the situation.

As described here, it is also possible to divide the situation where the surgical instrument is located inside the eye to be examined into the two situations: the situation in the middle of treatment; and the situation not in the middle of treatment and determine the two situations in addition to dividing the situation where the surgical instrument is located inside the eye to be examined into the three situations: the situation in the middle of treatment; the situation in the middle of insertion; and the situation in the middle of removal and determining the three situations. Additionally, it is also possible to divide such a situation into situations: a situation in the middle of insertion; and a situation other than the situation in the middle of insertion, determine the situations, and set the imaging condition on the basis of the determination result. Additionally, it is also possible to divide such a situation into situations: a situation in the middle of removal; and a situation other than the situation in the middle of removal, determine the situations, and set the imaging condition on the basis of the determination result.

Moreover, the example in which the focusing device controls the focal position of the transmission optical system in the above-mentioned embodiments has been shown, though not limited thereto.

For example, a microscope using the inner focus function may be used. In the microscope using the inner focus function, a focus adjusting lens is provided in the observation optical system. The driving of the focus adjusting lens can control the focal position of the transmission optical system without moving the microscope body up and down. In this case, the distance between the objective lens and the eye to be examined does not change.

Alternatively, as another example, the focal position of the transmission optical system may be controlled by moving at least one of the reduction lens or the front lens (wide-angle observation lens) constituting a part of the transmission optical system without moving the microscope body up and down.

It should be noted that the present technology may take the following configurations.

(1) A control device, including
a control unit that controls, on the basis of a detection result of a surgical instrument using a captured image of an eye to be examined which is imaged by an image pickup element of an ophthalmic microscope via a front lens, at least one of an imaging condition of the image pickup element or whether or not to perform inversion processing of making an image of a region inverted through the front lens a normal image.

(2) The control device according to (1), in which
the ophthalmic microscope includes an optical system that guides an image of the eye to be examined to the image pickup element and an extraocular illumination light source that outputs extraocular illumination light for illuminating the eye to be examined from outside, and
the imaging condition includes at least one of a focal position of the optical system or whether or not to perform radiation of the extraocular illumination light.

(3) The control device according to (1) or (2), in which
the control unit controls, on the basis of setting information preset for each situation determined on the basis of the detection result of the surgical instrument, the at least one of the imaging condition of the image pickup element or whether or not to perform the inversion processing.

(4) The control device according to (3), in which
in terms of the situation, in a case where it is detected that a tip of the surgical instrument is located outside a region of the front lens in the captured image, it is determined that it is a situation where an insertion position is being set, and in a case where it is detected that the tip of the surgical instrument is located inside the region of the front lens in the captured image, it is determined that it is a situation where the surgical instrument is located inside the eye to be examined.

(5) The control device according to (4), in which
the surgical instrument is insertable into the eye via a trocar placed on the eye to be examined, and
in terms of the setting information, in the situation where the insertion position is being set, the focal position is set to be on the trocar, the inversion processing is set not to be performed, and the extraocular illumination light is set to be output, and in the situation where the surgical instrument is being inserted, the focal position is set to be on the front lens, the inversion processing is set to be performed, and the extraocular illumination light is set not to be output.

(6) The control device according to (4) or (5), in which
the ophthalmic microscope further includes an intraocular illuminator that radiates intraocular illumination light to an inside of the eye to be examined,
the front lens is a wide-angle observation lens for observing the inside of the eye to be examined, and
in terms of the setting information, in the situation where the insertion position is being set, the intraocular illumination light is set not to be output, and in the situation where the surgical instrument is being inserted, the intraocular illumination light is set to be output.

(7) The control device according to any one of (1) to (5), in which
the front lens is a gonioscope for observing an angle of the eye to be examined.

(8) The control device according to any one of (3) to (7), further including
a memory that records resetting information obtained by the setting information preset for each situation being reset by a user of the ophthalmic microscope, in which
the control unit controls the imaging condition of the image pickup element by using the resetting information in preference to the preset setting information in accordance with the determined situation.

(9) The control device according to any one of (3) to (8), in which
the imaging condition includes at least one of a magnification of the optical system or a depth of field of the optical system, and
the control unit controls the at least one of the magnification or the depth of field on the basis of the setting information preset for each determined situation.

(10) The control device according to (9), in which
in terms of the situation, in a case where it is detected that a tip of the surgical instrument is located outside a region of the front lens in the captured image, it is determined that it is a situation where an insertion position is being set, and in a case where it is detected that the tip of the surgical instrument is located inside the region of the front lens in the captured image, it is determined that it is a situation where the surgical instrument is located inside the eye to be examined,
the situation where the surgical instrument is located inside the eye to be examined includes a situation in the middle of treatment where treatment of the eye to be examined is being performed and a situation not in the middle of treatment where the treatment of the eye to be examined is not being performed, and
the control unit controls the at least one of the magnification or the depth of field on the basis of the setting information preset for the determined situation in the middle of treatment or the determined situation not in the middle of treatment.

(11) The control device according to (10), in which
the situation not in the middle of treatment includes a situation in the middle of insertion that is a movement of the surgical instrument from the insertion position of the eye to be examined to a position for the treatment and a situation in the middle of removal that is a movement of the surgical instrument from the position for the treatment to the outside of the eye to be examined, and
the control unit controls the at least one of the magnification or the depth of field on the basis of the setting information preset for the determined situation in the middle of treatment, the determined situation in the middle of insertion, or the determined situation in the middle of removal.

(12) The control device according to any one of (3) to (11), in which
the ophthalmic microscope further includes an inverter that optically performs the inversion processing, and
the control unit controls the inverter on the basis of the setting information set for the determined situation.

(13) The control device according to any one of (3) to (11), further including
an image processing unit that performs the inversion processing of inverting a region in the captured image, in which an image is formed through the front lens, to thereby generate a display image, in which
the control unit controls the image processing unit on the basis of the setting information set for the determined situation.

(14) An ophthalmic microscope system, including:
an ophthalmic microscope including a front lens capable of being placed in front of an eye to be examined, an extraocular illumination light source that outputs extraocular illumination light for illuminating the eye to be examined from outside, and an image pickup element that images the eye to be examined; and
a control device that controls, on the basis of a detection result of a surgical instrument using a captured image of the eye to be examined which is imaged by the image pickup element via the front lens, at least one of an imaging condition of the image pickup element or whether or not to perform inversion processing of making an image of a region inverted through the front lens a normal image.

(15) An ophthalmic microscope, including:
a first optical system that transmits an image of an eye to be examined and includes a front lens that is placed in front of the eye to be examined;
a second optical system that transmits the image of the eye to be examined and does not include the front lens;
a first image pickup element on which the image of the eye to be examined, which is transmitted by the first optical system, is formed in a state in which a focal position of the first optical system is located in a region in which the front lens is located; and
a second image pickup element on which the image of the eye to be examined, which is transmitted by the second optical system, is formed in a state in which a focal position of the second optical system is located in a region outside a region of the eye to be examined, in which the front lens is located.

(16) The ophthalmic microscope according to (15), further including
a second illuminator that radiates second illumination light to the eye to be examined not via the front lens at a time of imaging with the second image pickup element.

(17) The ophthalmic microscope according to (15), further including:
a first illuminator that radiates first illumination light to an inside of the eye to be examined at a time of imaging with the first image pickup element; and
a second illuminator that radiates second illumination light to the eye to be examined at a time of imaging with the second image pickup element, in which
the imaging with the first image pickup element and the imaging with the second image pickup element are alternately performed,
the first illuminator outputs the first illumination light in synchronization with the imaging with the first image pickup element, and
the second illuminator outputs the second illumination light in synchronization with the imaging with the second image pickup element.

(18) The ophthalmic microscope according to (15), further including
a first illuminator that radiates first illumination light having a first wavelength to an inside of the eye to be examined at a time of imaging with the first image pickup element; and
a second illuminator that radiates second illumination light having a second wavelength different from the first wavelength to the eye to be examined at a time of imaging with the second image pickup element, in which
the first image pickup element includes an image pickup element that selectively receives light having the first wavelength and the second image pickup element includes an image pickup element that selectively receives light having the second wavelength.

(19) The ophthalmic microscope according to (15), further including:
a first illuminator that radiates first illumination light to an inside of the eye to be examined at a time of imaging with the first image pickup element; and
a second illuminator that radiates second illumination light having a second polarization state to the eye to be examined at a time of imaging with the second image pickup element, in which
an optical element that allows light having a first polarization state orthogonal to the second polarization state to pass therethrough is placed in front of the first image pickup element.

(20) An image processing apparatus, including
an image processing unit that combines a first image and a second image to thereby generate a display image, the first image being obtained by extracting a region of a first captured image, in which a front lens is located, and performing inversion processing only on the extracted region, the first captured image being acquired by a first image pickup element of an ophthalmic microscope, the second image being constituted by a region of a second captured image, which is other than the region in which the front lens is located, the second captured image being acquired by a second image pickup element of the ophthalmic microscope, the ophthalmic microscope including the front lens capable of being placed in front of an eye to be examined, the first image pickup element that adjusts a focal position onto the front lens and images the eye to be examined, and the second image pickup element that adjusts a focal position onto a region of the eye to be examined outside a region, in which the front lens is located and images the eye to be examined.

(21) An ophthalmic microscope system, including:
an ophthalmic microscope including
a front lens capable of being placed in front of an eye to be examined,
a first image pickup element that adjusts a focal position onto the front lens and images the eye to be examined, and
a second image pickup element that adjusts a focal position onto a region of the eye to be examined outside a region, in which the front lens is located and images the eye to be examined; and
an image processing apparatus including
an image processing unit that combines a first image and a second image to thereby generate a display image, the first image being obtained by extracting a region of a first captured image, in which the front lens is located, and performing inversion processing only on the extracted region, the first captured image being acquired by the first image pickup element, the second image being constituted by a region of a second captured image, which is other than the region in which the front lens is located, the second captured image being acquired by the second image pickup element.

REFERENCE SIGNS LIST 6 eye to be examined
10, 410 ophthalmic microscope
14 inverted image correction inverter
19 intraocular illuminator (first illuminator)
20 control device
24 control unit
25, 422 image processing unit
30, 430 transmission optical system (optical system)
50 trocar
100, 400 ophthalmic microscope system (microscope system)
132 wide-angle observation lens (front lens)
161 microscope illumination light source (extraocular illumination light source)
181 image pickup element
191 intraocular illumination light source
420 image processing device
431 intraocular transmission optical system (first optical system)
432 extraocular transmission optical system (second optical system)
4111 extraocular illumination light source
4181 intraocular observation image pickup element (first image pickup element)
4182 extraocular observation image pickup element (second image pickup element)
T surgical instrument

The invention claimed is:
1. A control device, comprising:
a control unit configured to:
acquire, from an ophthalmic microscope, an image of an eye under examination, wherein the ophthalmic microscope includes:
an image pickup element that captures the image; and
a front lens that inverts a first region in the captured image;
determine, based on the acquired image, whether a tip of a surgical instrument is present one of inside a second region in the acquired image, or outside of the second region, wherein the front lens is present in the second region;
in a case where the tip of the surgical instrument is present outside of the second region, determine a first situation indicating that an insertion position of the surgical instrument is being set;
acquire, based on the determination of the first situation, a first setting information associated with the first situation;
in a case where the tip of the surgical instrument is present inside the second region, determine a second situation indicating that the surgical instrument is inside the eye under examination;
acquire, based on the determination of the second situation, a second setting information associated with the second situation; and
control, based on one of the first setting information or the second setting information, at least one of:

an imaging condition of the image pickup element, or
an inversion process that inverts the inverted first region in the acquired image.

2. The control device according to claim 1, wherein the ophthalmic microscope further includes:
an optical system that guides the image to the image pickup element; and
an extraocular illumination light source that outputs extraocular illumination light to illuminate the eye under examination from an outside of the eye under examination, and
the imaging condition of the image pickup element includes at least one of a focal position of the optical system or the output of the extraocular illumination light.

3. The control device according to claim 2, wherein the surgical instrument is insertable into the eye under examination via a trocar,
the trocar is placed on the eye under examination,
the first setting information includes:
a first setting in which the focal position of the optical system is set to be on the trocar,
a second setting in which the inversion process is not executed, and
a third setting in which the extraocular illumination light is outputted, and
the second setting information includes:
a fourth setting in which the focal position of the optical system is set on the front lens,
a fifth setting in which the inversion process is executed, and
a sixth setting in which the extraocular illumination light is not outputted.

4. The control device according to claim 3, wherein the ophthalmic microscope further includes an intraocular illuminator that radiates intraocular illumination light to an inside of the eye under examination,
the front lens is a wide-angle observation lens that observes the inside of the eye under examination,
the first setting information further includes a seventh setting in which the intraocular illumination light is not outputted, and
the second setting information further includes an eighth setting in which the intraocular illumination light is outputted.

5. The control device according to claim 3, wherein the front lens is a gonioscope that observes an angle of the eye under examination.

6. The control device according to claim 5, wherein the second situation includes one of:
a third situation which indicates that the surgical instrument is inside the eye under examination in a case where a treatment of the eye under examination is being performed, or
a fourth situation which indicates that the surgical instrument is inside the eye under examination in a case where the treatment of the eye under examination is not being performed, and
the control unit is further configured to:
in a case where the second situation includes the third situation, acquire a third setting information associated with the third situation;
in a case where the second situation includes the fourth situation, acquire a fourth setting information associated with the fourth situation, wherein the second setting information includes at least one of the third setting information or the fourth setting information; and control the at least one of the magnification or the depth of field based on one of the third setting information or the fourth setting information.

7. The control device according to claim 2, wherein
the imaging condition further includes at least one of a magnification of the optical system or a depth of field of the optical system, and
the control unit is further configured to control the at least one of the magnification or the depth of field based on one of the first setting information or the second setting information.

8. The control device according to claim 7, wherein
a situation, the second situation includes one of:
  a third situation which indicates that the surgical instrument is inside the eye under examination in a case where a treatment of the eye under examination is being performed, or
  a fourth situation which indicates that the surgical instrument is inside the eye under examination in a case where the treatment of the eye under examination is not being performed,
the control unit is further configured to:
  in a case where the second situation includes the third situation, acquire a third setting information associated with the third situation;
  in a case where the second situation includes the fourth situation, acquire a fourth setting information associated with the fourth situation,
    wherein the second setting information includes at least one of the third setting information or the fourth setting information; and
  control the at least one of the magnification or the depth of field based on one of the third setting information or the fourth setting information.

9. The control device according to claim 8, wherein
the third situation includes one of:
  a fifth situation that indicates a first movement of the surgical instrument from the insertion position to a position for the treatment, or
  a sixth situation that indicates a second movement of the surgical instrument from the position for the treatment to an outside of the eye, and
the control unit is further configured to:
  in a case where the third situation includes the fifth situation, acquire a fifth setting information associated with the fifth situation;
  in a case where the third situation includes the sixth situation, acquire a sixth setting information associated with the sixth situation,
    wherein the third setting information includes at least one of the fifth setting information or the sixth setting information; and
  control the at least one of the magnification or the depth of field based on one of the fifth setting information or the sixth setting information.

10. The control device according to claim 2, wherein
the ophthalmic microscope further includes an inverter that optically executes the inversion process, and
the control unit is further configured to control the inverter based on one of the first setting information or the second setting information.

11. The control device according to claim 1, further comprising an image processing unit configured to:
  execute the inversion process; and
  generate a display image based on the inversion process,
wherein the control unit is further configured to control the image processing unit based on one of the first setting information or the second setting information.

12. An ophthalmic microscope system, comprising:
an ophthalmic microscope that includes:
  an extraocular illumination light source configured to output extraocular illumination light to illuminate an eye under examination from an outside of the eye under examination;
  an image pickup element configured to capture an image of the eye under examination; and
  a front lens configured to invert a first region in the captured image, wherein the front lens is in front of the eye; and
a control device configured to:
  acquire, from the ophthalmic microscope, the captured image of the eye under examination;
  determine, based on the acquired image, whether a tip of a surgical instrument is present one of inside a second region in the acquired image, or outside of the second region, wherein the front lens is present in the second region;
  in a case where the tip of the surgical instrument is present outside of the second region, determine a first situation indicating that an insertion position of the surgical instrument is being set;
  acquire, based on the determination of the first situation, a first setting information associated with the first situation;
  in a case where the tip of the surgical instrument is present inside the second region, determine a second situation indicating that the surgical instrument is inside the eye under examination;
  acquire, based on the determination of the second situation, a second setting information associated with the second situation; and
  control, based on one of the first setting information or the second setting information, at least one of:
    an imaging condition of the image pickup element, or
    an inversion process that inverts the inverted first region in the acquired image.

13. A control device, comprising:
a control unit configured to:
  acquire, from an ophthalmic microscope, an image of an eye under examination, wherein the ophthalmic microscope includes:
    an image pickup element that captures the image;
    a front lens that inverts a first region in the image;
    an optical system that guides the image to the image pickup element; and
    an extraocular illumination light source that outputs extraocular illumination light to illuminate the eye under examination from an outside of the eye under examination;
  determine, based on the acquired image, whether a tip of a surgical instrument is present one of inside a second region in the acquired image, or outside of the second region, wherein the front lens is present in the second region;
  in a case where the tip of the surgical instrument is present outside of the second region, determine a first situation indicating that an insertion position of the surgical instrument is being set;

acquire, based on the determination of the first situation, a first setting information associated with the first situation;

in a case where the tip of the surgical instrument is present inside the second region, determine a second situation indicating that the surgical instrument is inside the eye under examination;

acquire, based on the determination of the second situation, a second setting information associated with the second situation, wherein
the surgical instrument is inserted into the eye via a trocar, and
the trocar is placed on the eye; and control, based on one of the first setting information or the second setting information, at least one of:
an imaging condition of the image pickup element, or
an inversion process that inverts the inverted first region in the captured image, wherein
the imaging condition of the image pickup element includes at least one of a focal position of the optical system or the output of the extraocular illumination light by the extraocular illumination light source, the first setting information includes:
a first setting in which the focal position of the image pickup element is set on the trocar;
a second setting in which the inversion process is not executed; and
a third setting in which the extraocular illumination light is outputted, and the second setting information includes:
a fourth setting in which the focal position of the image pickup element is set on the front lens;
a fifth setting in which the inversion process is executed; and
a sixth setting in which the extraocular illumination light is not outputted.

* * * * *